(12) United States Patent
Lee et al.

(10) Patent No.: US 12,089,962 B2
(45) Date of Patent: Sep. 17, 2024

(54) METHOD AND DEVICE FOR MEASURING BIOSIGNAL BY USING ELECTRODE

(71) Applicant: Samsung Electronics Co., Ltd., Gyeonggi-do (KR)

(72) Inventors: Suho Lee, Gyeonggi-do (KR); Younghyun Kim, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 612 days.

(21) Appl. No.: 17/420,807

(22) PCT Filed: Oct. 28, 2019

(86) PCT No.: PCT/KR2019/014306
§ 371 (c)(1),
(2) Date: Jul. 6, 2021

(87) PCT Pub. No.: WO2020/145494
PCT Pub. Date: Jul. 16, 2020

(65) Prior Publication Data
US 2022/0087615 A1    Mar. 24, 2022

(30) Foreign Application Priority Data
Jan. 11, 2019 (KR) .................. 10-2019-0003666

(51) Int. Cl.
*A61B 5/00* (2006.01)
*A61B 5/24* (2021.01)
(Continued)

(52) U.S. Cl.
CPC .............. *A61B 5/7225* (2013.01); *A61B 5/24* (2021.01); *A61B 5/256* (2021.01); *A61B 5/279* (2021.01);
(Continued)

(58) Field of Classification Search
CPC ... A61B 5/25; A61B 5/7203; A61B 2562/182; A61B 5/30; A61B 5/302; A61B 5/369;
(Continued)

(56) References Cited

U.S. PATENT DOCUMENTS 5,876,351 A * 3/1999 Rohde .................... A61B 5/339
600/509
10,709,339 B1 * 7/2020 Lusted ................... A61B 5/282
(Continued)

FOREIGN PATENT DOCUMENTS

KR  2003-0063640 A  7/2003
KR  10-2009-0034647 A  4/2009
(Continued)

OTHER PUBLICATIONS

Grimbergen et al. (High-quality recording of bioelectric events: part 1 interference reduction, theory and practice, 1990). (Year: 1990).*
(Continued)

Primary Examiner — Mohammad K Islam
(74) Attorney, Agent, or Firm — Cha & Reiter, LLC

(57) ABSTRACT

Disclosed in various embodiments of the present invention are a method and a device comprising: a first electrode, a second electrode and a third electrode which make contact with the body of a user; an instrumentation amplifier for differentially amplifying signals received from the first electrode and the second electrode; a feedback amplifier for feeding back feedback noise to the body of the user through the third electrode; and a control circuit, wherein the control circuit is configured to analyze a noise level by using a biosignal obtained from the instrumentation amplifier, and control the gain of the feedback amplifier on the basis of the result of the analysis. Various embodiments are possible.

13 Claims, 18 Drawing Sheets

(51) Int. Cl.
*A61B 5/256* (2021.01)
*A61B 5/279* (2021.01)
*H03F 1/34* (2006.01)

(52) U.S. Cl.
CPC ........ *H03F 1/34* (2013.01); *A61B 2560/0468* (2013.01)

(58) Field of Classification Search
CPC ....... A61B 5/389; A61B 5/681; A61B 5/7225; A61B 2562/0209; A61B 2562/046; A61B 5/0006; A61B 5/024; A61B 5/0245; A61B 5/053; A61B 5/0531; A61B 5/0537; A61B 5/282; A61B 5/291; A61B 5/296; A61B 5/6801; A61B 5/6843; A61B 5/7214; A61B 2560/0204; A61B 2562/0215; A61B 2562/043; A61B 2562/166; A61B 5/0002; A61B 5/0028; A61B 5/01; A61B 5/02; A61B 5/0205; A61B 5/02416; A61B 5/02438; A61B 5/02444; A61B 5/026; A61B 5/0261; A61B 5/0285; A61B 5/121; A61B 5/14542; A61B 5/14551; A61B 5/301; A61B 5/304; A61B 5/305; A61B 5/31; A61B 5/318; A61B 5/346; A61B 5/349; A61B 5/38; A61B 5/398; A61B 5/4266; A61B 5/4869; A61B 5/4875; A61B 5/4878; A61B 5/6802; A61B 5/6822; A61B 5/6823; A61B 5/6824; A61B 5/6826; A61B 5/6828; A61B 5/6829; A61B 5/683; A61B 5/685; A61B 5/6885; A61B 5/6898; A61B 5/7207; A61B 5/7232; A61B 5/24; A61B 5/256; A61B 5/279; A61B 2560/0468; H03F 1/34; H03F 2203/45136; H03F 3/45475; H03F 1/26

See application file for complete search history.

(56) References Cited

U.S. PATENT DOCUMENTS

| | | |
|---|---|---|
| 2003/0139654 A1 | 7/2003 | Kim et al. |
| 2005/0215916 A1 | 9/2005 | Fadem et al. |
| 2007/0078324 A1 | 4/2007 | Wijisiriwardana |
| 2007/0167694 A1* | 7/2007 | Causevic ............... A61B 5/384 600/544 |
| 2008/0077039 A1* | 3/2008 | Donnett ............... A61B 5/4094 600/544 |
| 2010/0249635 A1* | 9/2010 | Van Der Reijden ..... A61B 5/38 600/544 |
| 2011/0306892 A1 | 12/2011 | Kim et al. |
| 2012/0232369 A1* | 9/2012 | Kim ........................ A61B 5/30 600/372 |
| 2017/0105646 A1* | 4/2017 | Bryenton ............... A61B 5/346 |

FOREIGN PATENT DOCUMENTS

| | | |
|---|---|---|
| KR | 10-2011-0111064 A | 10/2011 |
| KR | 10-2011-0135296 A | 12/2011 |
| KR | 10-2012-0102444 A | 9/2012 |
| KR | 10-2015-0057388 A | 5/2015 |
| KR | 10-2016-0066081 A | 6/2016 |

OTHER PUBLICATIONS

Korean Office Action dated Nov. 22, 2023.

* cited by examiner

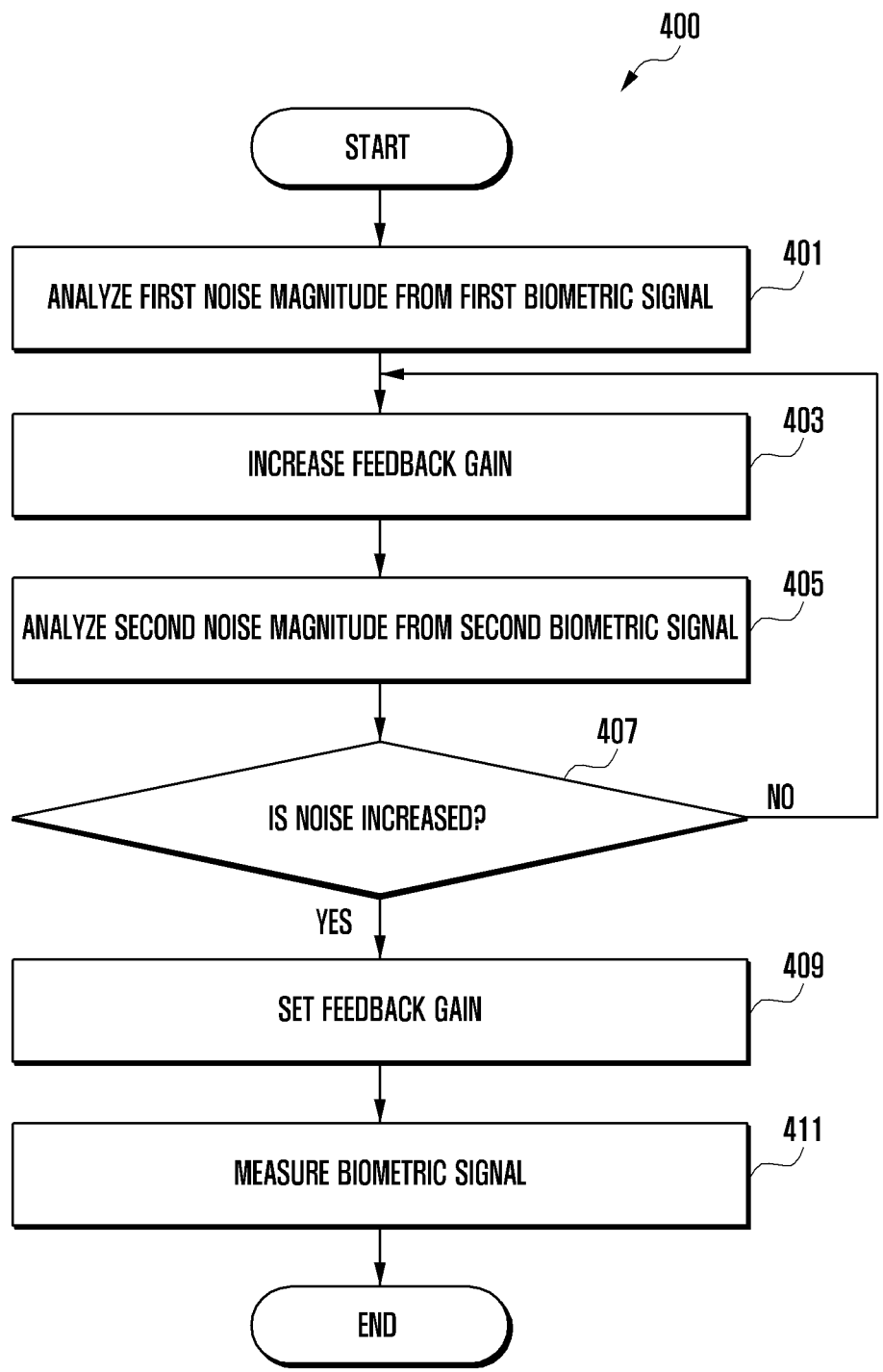

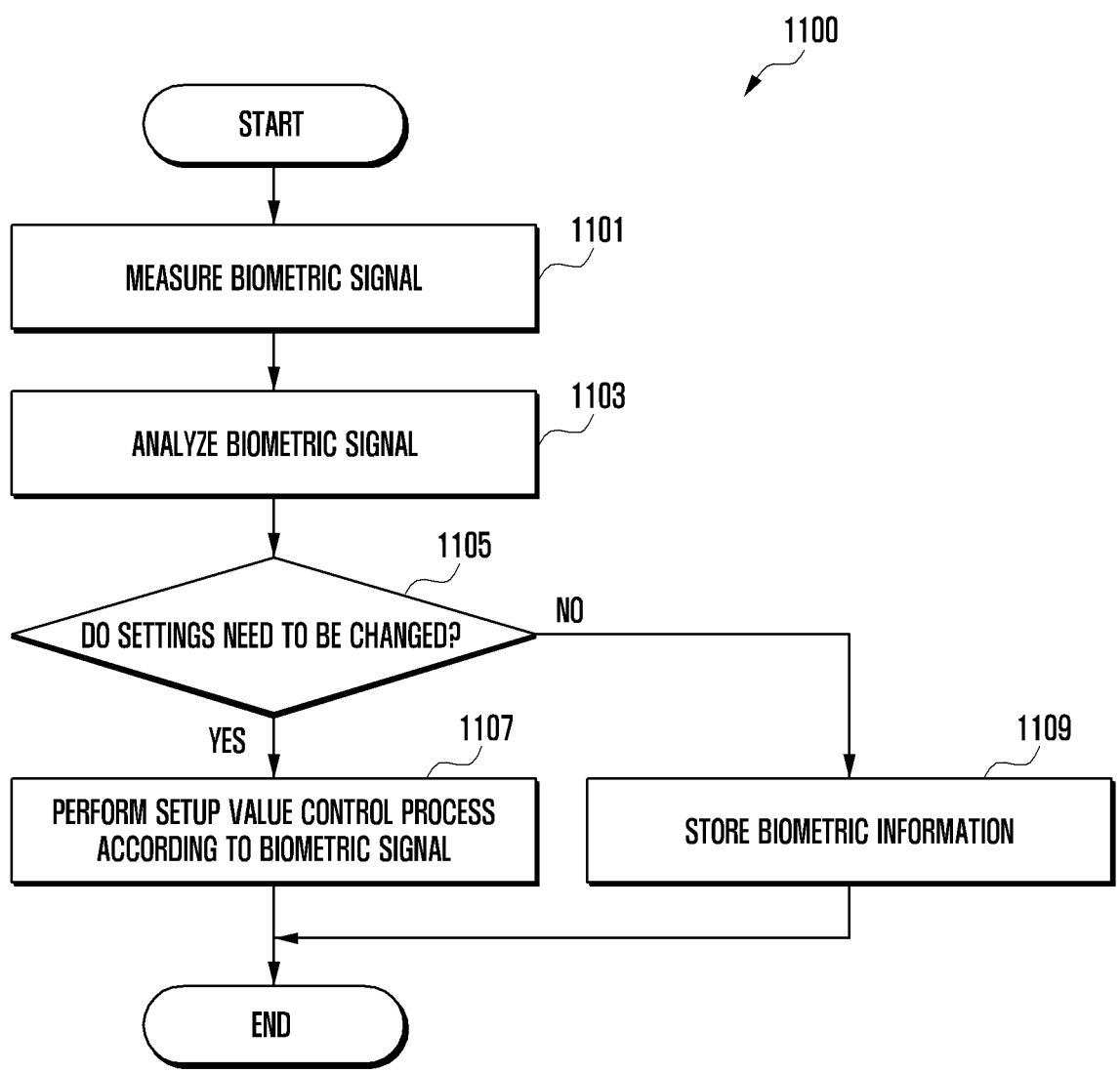

# METHOD AND DEVICE FOR MEASURING BIOSIGNAL BY USING ELECTRODE

CROSS REFERENCE TO RELATED APPLICATIONS

This application is a National Phase Entry of PCT International Application No. PCT/KR2019/014306, which was filed on Oct. 28, 2019, and claims a priority to Korean Patent Application No. 10-2019-0003666, which was filed on Jan. 11, 2019, the contents of which are incorporated herein by reference.

TECHNICAL FIELD

The disclosure relates to a method and apparatus for measuring a biometric signal using an electrode.

BACKGROUND ART

Recently, with the development of digital technologies, various types of electronic devices are being widely utilized, such as, mobile communication terminals, personal digital assistants (PDA), electronic organizers, smart phones, tablet personal computers (PC), wearable devices, and the like. Further, hardware parts and/or software parts of an electronic device have been continuously improved in order to support and increase the functions of the electronic device.

For example, the electronic device includes an electrode for measuring a biometric signal, and may obtain a biometric signal such as an electrocardiogram (ECG), electroencephalogram (EEG), an electromyography (EMG) using an electrode.

DISCLOSURE OF INVENTION

Technical Problem

A biometric signal may be affected by various factors including a surrounding environment, such as temperature, humidity, and electromagnetic waves, the emotional state of a user, or the like. The conventional art which measures a biometric signal using an electrode uses a scheme that post-processes a signal obtained from an electrode using an initially set gain or size of the electrode, irrespective of a change of the biometric signal. The conventional art may be highly dependent upon a signal obtained from an electrode, and if a noise component gets into a biometric signal, the conventional art may be incapable of removing the noise component. In order to reduce a noise component in a biometric signal, an electronic device may perform negative feedback of a common noise component to a body part. In this instance, as the gain of a feedback amplifier is increased, a common noise component is decreased. However, the noise component may not be decreased any longer if the gain is greater than or equal to a predetermined gain.

According to certain embodiments, there is provided a method and apparatus for effectively removing a noise component by adjusting a noise feedback gain according to an environment that varies or by changing the contact area of an electrode (e.g., the number of electrode nodes included in an electrode) or the locations of the electrode nodes included in an electrode.

Solution to Problem

In accordance with an aspect of the disclosure, an electronic device may include: a first electrode, a second electrode, and a third electrode which are in contact with a body part of a user; an instrumentation amplifier which differentially amplifies signals received from the first electrode and the second electrode; a feedback amplifier which feeds back a feedback noise to a body part of the user via the third electrode; and a control circuit, wherein the control circuit is configured to analyze the magnitude of noise using a biometric signal obtained from the instrumentation amplifier, and to control the gain of the feedback amplifier based on a result of the analysis.

In accordance with an aspect of the disclosure, an electronic device may include: a first electrode, a second electrode, and a third electrode which are in contact with a body part of a user; a multiplexer connected to the first electrode and the second electrode in parallel; an instrumentation amplifier which differentially amplifies a signal output from the multiplexer; a feedback amplifier which feeds back a feedback noise to a body part of the user via the third electrode; and a control circuit, wherein the control circuit is configured to analyze the magnitude of noise using the signal output from the multiplexer, and to adjust the area of the first electrode and the area of the second electrode based on a result of the analysis.

In accordance with an aspect of the disclosure, an operation method of an electronic device including a first electrode, a second electrode, and a third electrode includes: obtaining, using an instrumentation amplifier, a biometric signal from signals received from the first electrode and the second electrode; feeding back a feedback noise to a body part of a user via the third electrode using a feedback amplifier; analyzing the magnitude of noise using the biometric signal; and controlling the gain of the feedback amplifier based on a result of the analysis.

Advantageous Effects of Invention

According to certain embodiments, a noise component can be effectively removed by adjusting a noise feedback gain according to an environment that varies or by changing the contact area of an electrode (e.g., the number of electrode nodes included in an electrode) or the location of an electrode node included in an electrode.

According to certain embodiments, a signal to noise ratio (SNR) of a biometric signal can be increased by reducing noise of a biometric signal, and thus, a biometric signal with a good quality can be obtained.

BRIEF DESCRIPTION OF DRAWINGS

FIG. 4 is a flowchart 400 illustrating a method of measuring a biometric signal using an electrode by an electronic device according to certain embodiments;

FIG. 11 is a flowchart 1100 illustrating a method of measuring a biometric signal using an electrode by an electronic device according to certain embodiments.

MODE FOR CARRYING OUT THE INVENTION

Figure 1:
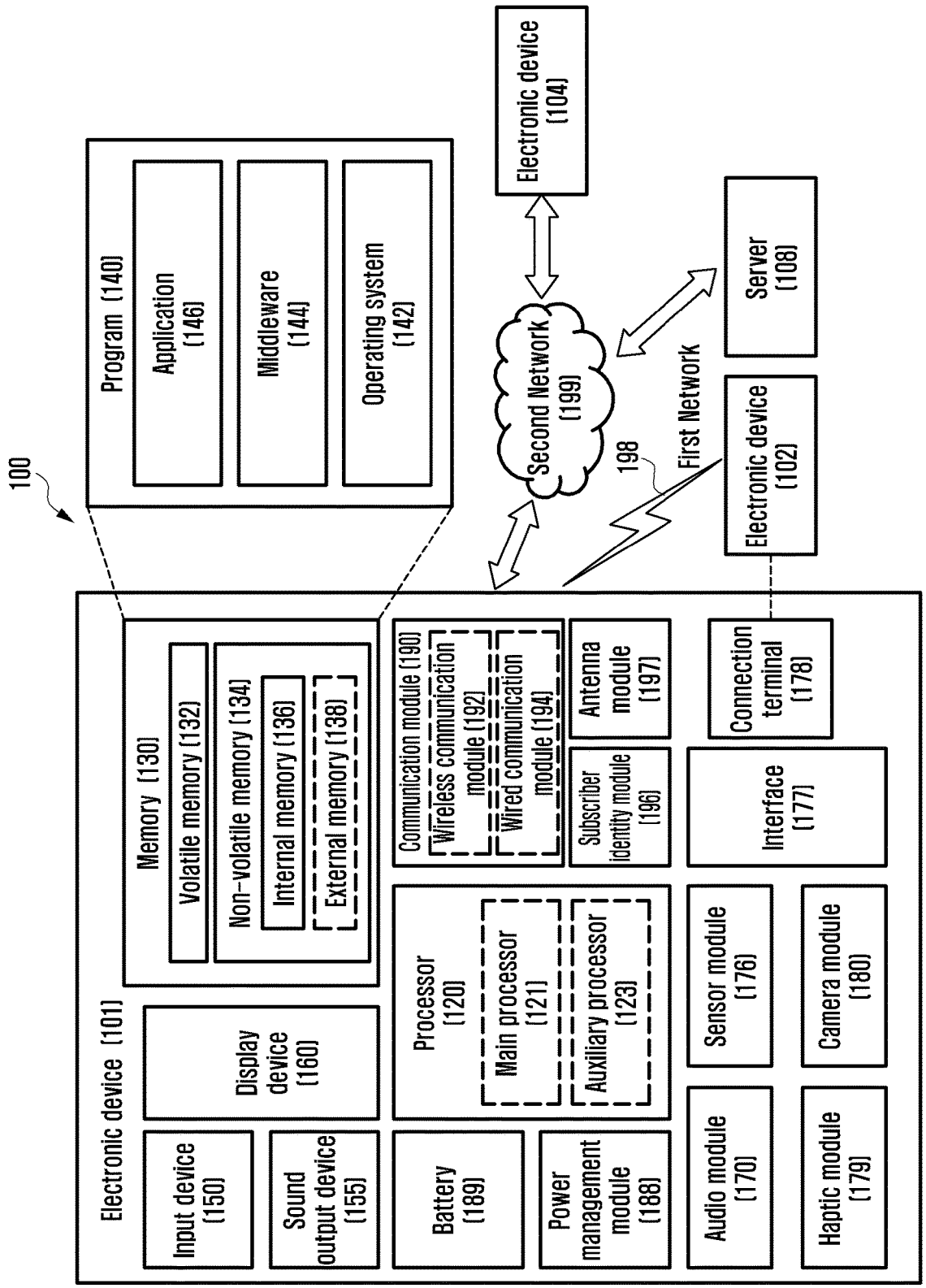
FIG. 1 is a block diagram of an electronic device 101 in a network environment 100 according to certain embodiments.

It should be appreciated that certain embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), the element may be coupled with the other element directly (e.g., wiredly), wirelessly, or via a third element.

As used herein, the term "module" may include a unit implemented in hardware, software, or firmware, or any combination thereof, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

FIG. 1 is a block diagram illustrating an electronic device 101 in a network environment 100 according to certain embodiments.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108.

According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to an example embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, or a keyboard.

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector), The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an example embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include one or more antennas, and, therefrom, at least one antenna appropriate for a communication scheme used in the communication network, such as the first network 198 or the second network 199, may be selected, for example, by the communication module 190 (e.g., the wireless communication module 192). The signal or the power may then be transmitted or received between the communication module 190 and the external electronic device via the selected at least one antenna.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Certain embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the "non-transitory" storage medium is a tangible device, and may not include a signal (e.g., an electromagnetic wave), but this term does not differentiate between where data is semi-permanently stored in the storage medium and where the data is temporarily stored in the storage medium.

According to an embodiment, a method according to certain embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to certain embodiments, each component (e.g., a module or a program) of the above-described components may include a single entity or multiple entities. According to certain embodiments, one or more of the above-described components may be omitted, or one or more other components may be added. Alternatively or additionally, a plurality of components (e.g., modules or programs) may be integrated into a single component. In such a case, according to certain embodiments, the integrated component may still perform one or more functions of each of the plurality of components in the same or similar manner as they are performed by a corresponding one of the plurality of components before the integration. According to certain embodiments, operations performed by the module, the program, or another component may be carried out sequentially, in parallel, repeatedly, or heuristically, or one or more of the operations may be executed in a different order or omitted, or one or more other operations may be added.

Figure 2A:
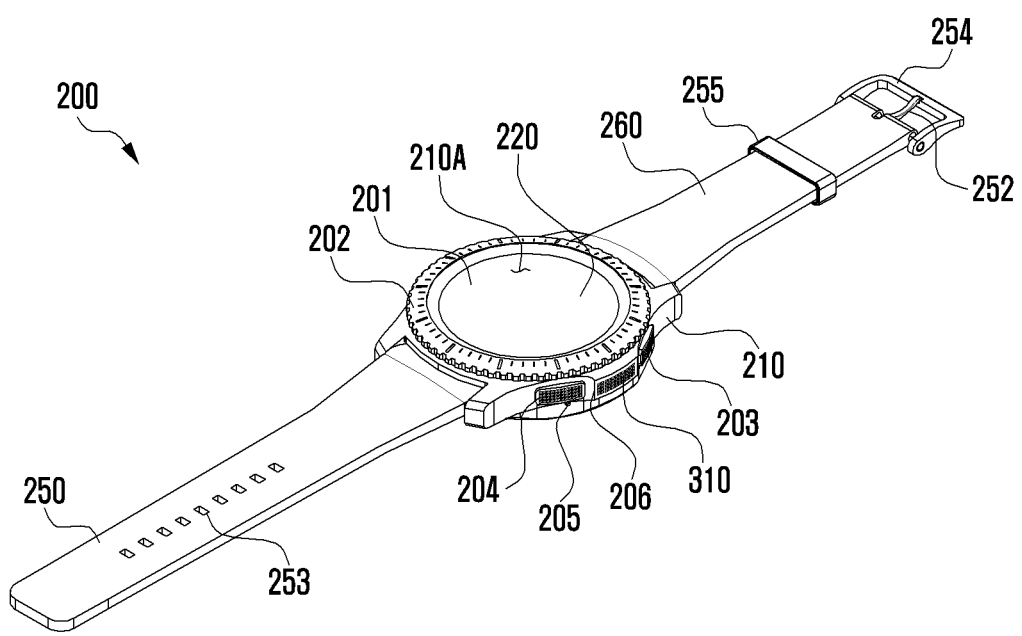
FIGS. 2A and 2B are the front view and back view of an electronic device 200 according to certain embodiments.
Figure 2B:
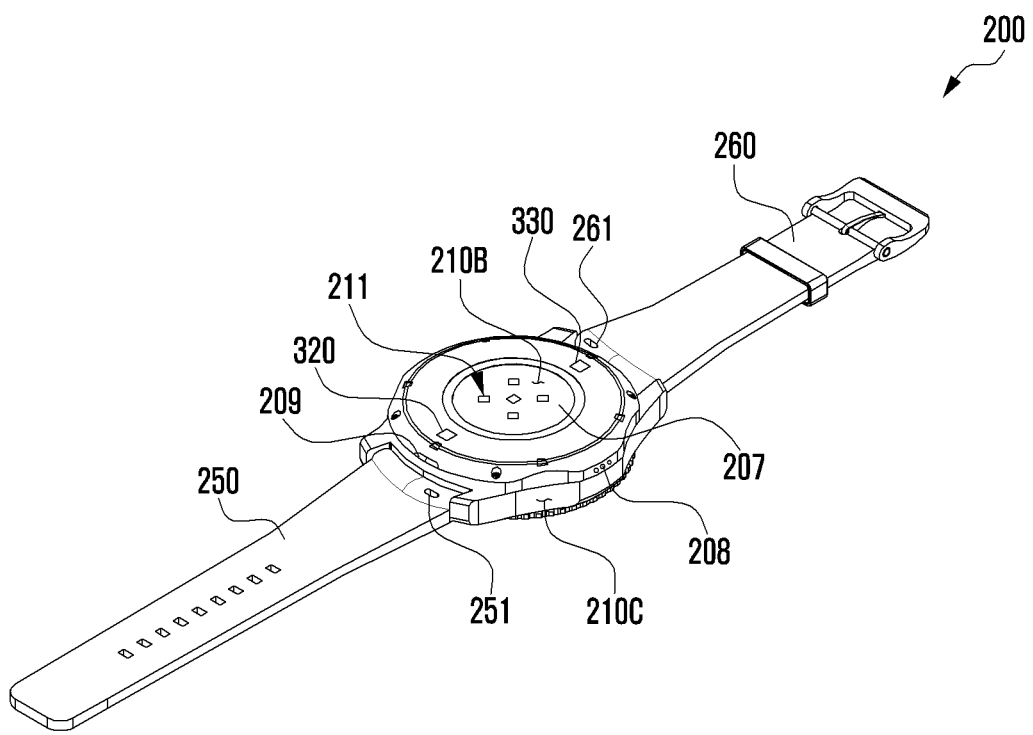

FIG. 2A is a front perspective view illustrating an example electronic device 200 according to certain embodiments, and FIG. 2B is a rear perspective view illustrating the example electronic device 200 according to certain embodiments.

Referring to FIGS. 2A and 2B, an electronic device 200 according to an embodiment (e.g., an electronic device 101 of FIG. 1) may include a housing 210 including a first surface (or a front surface) 210A, a second surface (or a rear surface) 210B, and a side surface 210C that surrounds a space between the first surface 210A and the second surface 210B, and fastening members 250 and 260 (e.g., straps) connected to at least portions of the housing 210 and configured to detachably fasten the electronic device 200 to a portion (e.g., a wrist, or an ankle) of the body of a user. In another embodiment (not illustrated), the housing may refer to a structure that defines some of the first surface 210A, the second surface 210B, and the side surface 210C of FIG. 2A.

According to an embodiment, the first surface 210A may be defined by a front plate 201 (e.g., a glass plate or a polymer plate including various coating layers), at least a portion of which is substantially transparent. The second surface 210B may be defined by a rear plate 207 that is substantially opaque. The rear plate 207, for example, may be formed of coated or colored glass, ceramics, a polymer, a metal (e.g., aluminum, stainless steel (STS), or magnesium), or a combination of at least two thereof. The side surface 210C may be coupled to the front plate 201 and the rear plate 207, and may be defined by a side bezel structure (or 'a side member') 206 including a metal and/or a polymer.

In some embodiments, the rear plate 207 and the side bezel structure 206 may be integrally formed and may include the same material (e.g., a metallic material such as aluminum). The fastening members 250 and 260 may be formed of various materials and may have various shapes. A single body or a plurality of unit links that may move with respect to each other may be formed of woven fabric, leather, rubber, urethane, a metal, ceramics, or a combination of at least two thereof.

According to an embodiment, the electronic device 200 may include at least one of a display 220 (e.g., a display device 160 of FIG. 1), audio modules 205 and 208, a sensor module 211, key input devices 202, 203, and 204, and a connector hole 209. In some embodiments, at least one (e.g., the key input devices 202, 203, and 204, the connector hole 209, or the sensor module 211) of the elements may be omitted from the electronic device 200 or another component may be additionally included in the electronic device 200.

The display 220 (e.g., the display device 160 of FIG. 1, or a user interface), for example, may be exposed through a first part (e.g., a corresponding part of the front plate 201). The shape of the display 220 may correspond to the shape of the front plate 201, and may include various shapes, such as a circular shape, an elliptical shape, or a polygonal shape. The display 220 may be coupled to or be disposed to be adjacent to a touch detection circuit, a pressure sensor that may measure the strength (the pressure) of a touch, and/or a fingerprint sensor.

The audio modules 205 and 208 may include a microphone hole 205 and a speaker hole 208. A microphone for acquiring external sounds may be disposed in the microphone hole 205, and in some embodiments, a plurality of microphones may be disposed to detect the direction of a sound. The speaker hole 208 may be used for an external speaker and a communication receiver. In some embodiments, the speaker holes 207 and the microphone hole 203 may be realized by one hole or a speaker may be included while the speaker holes 207 are not employed (e.g., a piezoelectric speaker).

The sensor module 211 may produce an electric signal or a data value corresponding to an internal operational state of the electronic device 200 or an electric signal or a data value corresponding to the external environment state. The sensor module 211 may be exposed via, for example, a second side 210B of a housing 210, and may include a biometric sensor module (e.g., a HRM sensor). The sensor module 100 may further include at least one sensor module which is not illustrated, for example, a gesture sensor, a gyro sensor, a pressure sensor, a magnetic sensor, an acceleration sensor, a grip sensor, a color sensor, an infrared (IR) sensor, a biometric sensor, a temperature sensor, a humidity sensor, or an illumination sensor.

A first electrode 310 may be disposed in a lateral bezel structure 206, and a second electrode 320 and a third electrode 330 may be disposed in the second side 210B. The first electrode 310 to the third electrode 330 may measure at least one of electrocardiogram (ECG), galvanic skin response (GSR), electroencephalogram (EEG), or bioimpedance assessment (BIA). Although it is illustrated that three electrodes are present in the drawing, three or more electrodes may be used.

The key input devices 202, 203, and 204 may include a wheel key 202 disposed on the first surface 210A of the housing 210 and being rotatable in at least one direction, and/or side key buttons 202 and 203 disposed on the side surface 210C of the housing 210. The wheel key may have a shape corresponding to the shape of the front plate 210. In another embodiment, the electronic device 200 may not include some or all of the above-mentioned key input devices 202, 203, and 204, and the key input devices 202, 203, and 204 which are not included, may be realized in different forms, such as a soft key, on the display 220. The connector hole 209 may accommodate a connector (e.g., a USB connector) for transmitting and receiving power and/or data to and from an external electronic device, and may include another connector hole (not illustrated) that may accommodate a connector for transmitting and receiving an audio signal to and from an external electronic device. The electronic device 200, for example, may further include a connector cover (not illustrated) configured to cover at least a portion of the connector hole 209 to prevent introduction of external foreign substances through the connector hole 109.

The fastening members 250 and 260 may be detachably fastened to at least a partial area of the housing 210 using locking members 251 and 261. The fastening members 250 and 260 may include one or more of a fixing member 252, a fixing member coupling hole 253, a band guide member 254, and a band fixing ring 255.

The fixing member 252 may be configured to fix the housing 210 and the fastening members 250 and 260 to a portion (e.g., a wrist or a wrinkle) of the body of the user. The fixing member coupling hole 253 may fix the housing 210 and the fastening members 250 and 260 to a portion of the body of the user in correspondence to the fixing member 252. The band guide member 254 may be configured to restrict a motion range of the fixing member 252 when the fixing member 252 is coupled to the fixing member coupling hole 253 so that the fastening members 250 and 260 are fastened to be attached to a portion of the body of the user. The band fixing ring 255 may restrict motion ranges of the fastening members 250 and 260 in a state in which the fixing member 252 and the fixing member coupling hole 253 are coupled to each other.

Figure 3A:
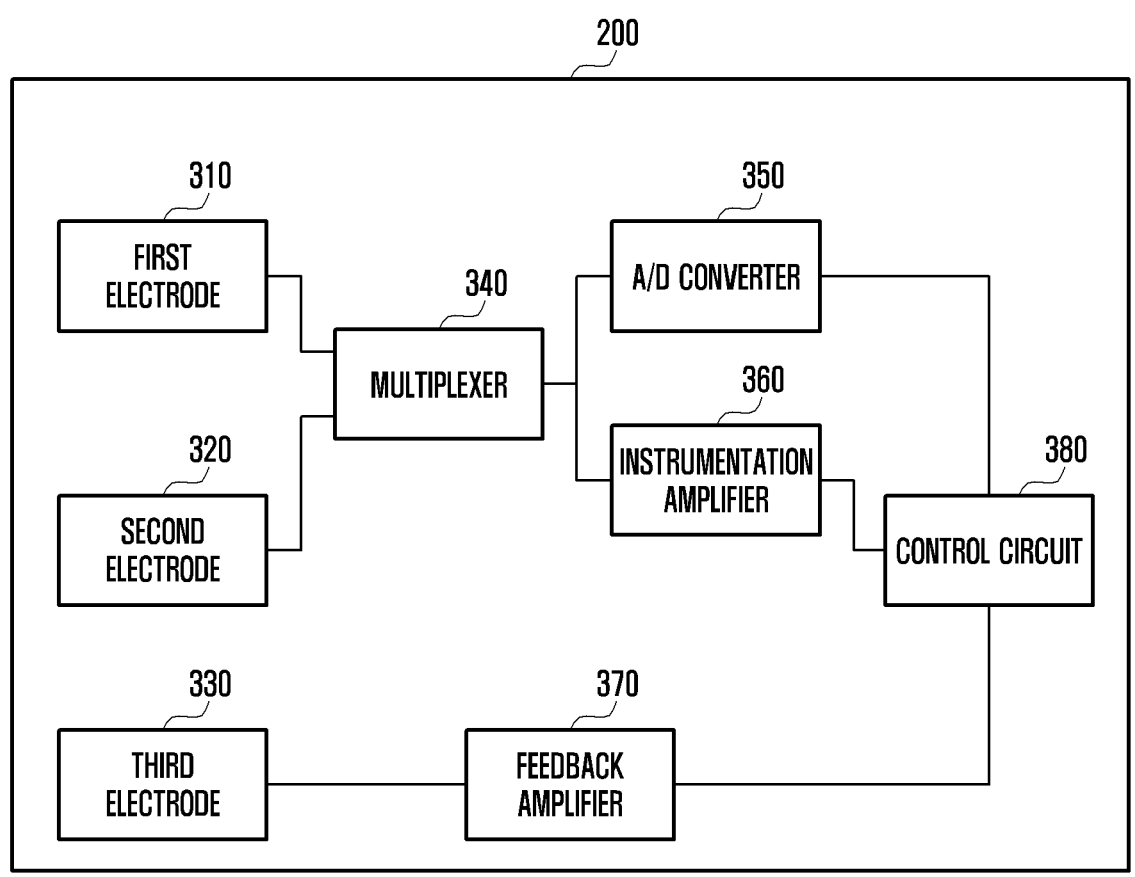
FIGS. 3A and 3B are block diagrams illustrating the configuration of the electronic device 200 according to certain embodiments.
Figure 3B:
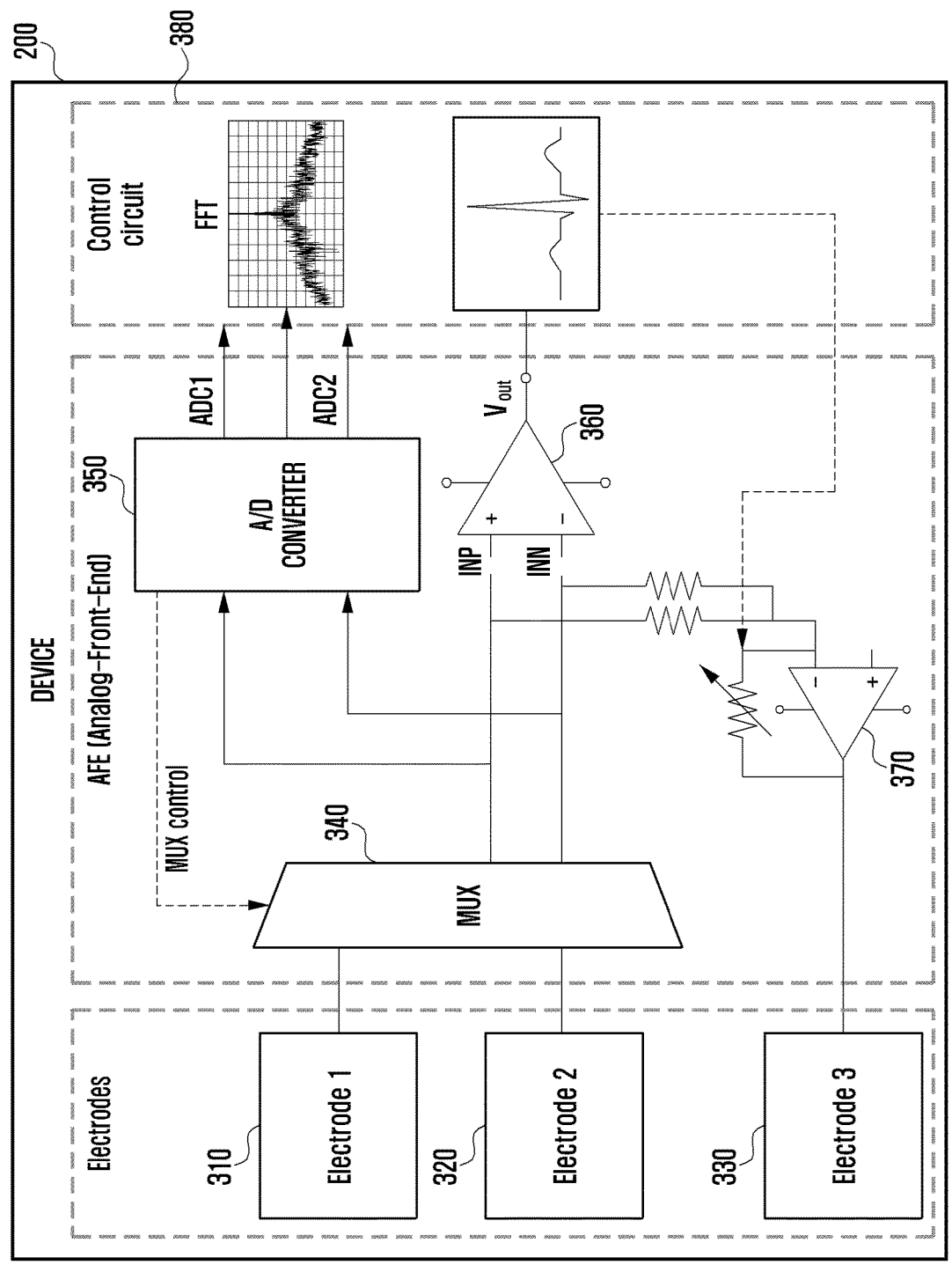

FIGS. 3A and 3B are block diagrams illustrating the configuration of the electronic device 200 according to certain embodiments.

Referring to FIGS. 3A and 3B, the electronic device 200 (e.g., the electronic device 101 of FIG. 1) according to certain embodiments may include the first electrode 310, the second electrode 320, the third electrode 330, a multiplexer 340, an A/D converter 350, an instrumentation amplifier 360, a feedback amplifier 370, and a control circuit 380.

The first electrode 310 and the second electrode 320 may primarily receive a biometric signal from a body part of a user. The third electrode 330 may provide a noise signal as feedback to a body part of the user. According to various embodiments, the first electrode 310 to the third electrode 330 may be formed of a conductive material, and a current may flow through the first electrode 310 to the third electrode 330. For example, the first electrode 310 to the third electrode 330 may be formed of conductive fibers or metal having low resistance such as stainless steel or gold.

The first electrode 310 to the third electrode 330 may produce contact impedance when being in contact with skin (or body part) of a user. The first electrode 310 to the third electrode 330 may directly flow electric charges to a body part of a user. Alternatively, the first electrode 310 and the second electrode 320 may measure an output value based on a capacitance value between electric charges and a body part of the user. The first electrode 310 to the third electrode 330 may measure at least one biometric signal among electrocardiogram (ECG), galvanic skin response (GSR), electroencephalogram (EEG), or bioimpedance assessment (BIA).

The first electrode 310 and the second electrode 320 may be provided in the forms of N×M matrices (N and M are natural numbers). N and M may be identical to, or different from each other. If the first electrode 310 and the second electrode 320 are provided in the forms of matrices, the output node of each of the first electrode 310 and the second electrode 320 may be connected to an input node of the multiplexer 340. Regarding the first electrode 310 and the second electrode 320, the number (or the area) of electrode nodes or the locations of the electrode nodes included in the first electrode 310 and the second electrode 320 may be changed, as controlled by the multiplexer 340.

The first electrode 310 may be disposed in the foreside (e.g., the first side 210A of FIGS. 2A and 2B) or a lateral side (e.g., the lateral bezel structure 206 of FIGS. 2A and 2B) of the electronic device 200, and the second electrode 320 and the third electrode 330 may be provided in the rear side (e.g., the second side 210B of FIGS. 2A and 2B) of the electronic device 200. For example, if a user wears the electronic device 200 on his or her wrist, the second electrode 320 and the third electrode 330 may be in contact with the wrist of the user, and the first electrode 310 may be in contact with a body part of the user depending on the intention of the user. The user may wear the electronic device 200 on his or her left wrist, and may make a contact of his or her finger with the first electrode 310. The first electrode 310 and the second electrode 320 may be connected to an input of the multiplexer, and the third electrode 330 may be connected to the output of the feedback amplifier 370.

The first electrode 310 and the third electrode 330 may be disposed in the first side 210A of the electronic device 200, and the second electrode 320 may be provided in the second side 210B of the electronic device 200. For example, if a user wears the electronic device 200 on his or her wrist, the second electrode 320 may be in contact with the wrist of the user, and the first electrode 310 and the third electrode 330 may be in contact with a body part of the user depending on the intention of the user. The user may wear the electronic device 200 on his or her left wrist, and may make a contact of his or her right finger with the first electrode 310 and the third electrode 330.

The multiplexer 340 may be a combination circuit that selects one of multiple input lines and connects the selected input line to a uni-output line. The multiplexer 340 is simply called "MUX", and is also referred to as a "data selector" since the multiplexer 340 receives multiple input data and provides a single output. The multiplexer 340 may be connected between the first and second electrodes 310 and 320 and the instrumentation amplifier 360. The multiplexer 340 may be connected in parallel with the first electrode 310 and the second electrode 320. The multiplexer 340 may transfer all signals input from the first electrode 310 and second electrode 320 to the instrumentation amplifier 360, or may transfer some of the signals input from the first electrode 310 and the second electrode 320 to the instrumentation amplifier 360. According to certain embodiments, the multiplexer 340 may control the number (area) of electrode nodes or the locations of the electrode nodes included in the first electrode 310 and the second electrode 320 according to the magnitude of noise or the magnitude of a contact impedance.

If the first electrode 310 and the second electrode 320 are provided in the forms of matrices, an input node of the multiplexer 340 may be connected to the output node of each of the first electrode 310 and the second electrode 320. The multiplexer 340 may transfer all signals input via input nodes to the output node, or may transfer some of the signals input via the input nodes to the output node, as controlled by the control circuit 380. The multiplexer 340 may transfer all signals obtained from the first electrode 310 and the second electrode 320 to the instrumentation amplifier 360, or may transfer some of the signals obtained from the first electrode 310 and the second electrode 320 to the instrumentation amplifier 360.

An analog/digital (A/D) converter (ADC) 350 may convert an analog signal into a digital signal. The A/D converter 350 may convert an analog signal output from the multiplexer 340 into a digital signal and may provide the digital signal to the control circuit 380. The A/D converter 350 may convert a first input signal and a second input signal output from the multiplexer 340 into a first digital signal and a second digital signal, respectively.

The instrumentation amplifier 360 may be a circuit appropriate for detecting or amplifying a small difference when a single signal or two or more different signals overlap. The instrumentation amplifier 360 may be a circuit including at least three operational amplifiers. The instrumentation amplifier 360 may differentially amplify signals output from the multiplexer 340, and may remove a noise component so as to produce a biometric signal. The instrumentation amplifier 360 may differentially amplify signals input to a positive input and a negative input. Although not illustrated in the drawing, the electronic device 200 may further include a filter in order to obtain a biometric signal from which a noise component (or signal) is removed.

The feedback amplifier 370 may perform negative feedback of a part of an output signal, that is, may return the part of the output signal as an input in an opposite phase so as to reduce a strain or noise of the output, and to increase stability. The feedback amplifier 370 may input a signal output from the multiplexer 340 as a positive input, may input a reference voltage (e.g., Vref) as a negative input, and may output a feedback signal to the third electrode 330. The signal output from the multiplexer 340 may be input to the feedback amplifier 370 as a positive input in parallel. The feedback signal may be provided to the body of a user via the third electrode 330. The feedback amplifier 370 may feed back a power source noise component (e.g., 50 to 60 Hz) to the body of the user, so as to reduce (or remove) the power source noise component.

The control circuit 380 may analyze the magnitude of noise using a biometric signal obtained from the instrumentation amplifier 360. The control circuit 380 may obtain the biometric signal by increasing a gain (a gain value or a feedback gain) of the feedback amplifier 370. The gain may be a degree by which the feedback amplifier 370 amplifies a signal. The control circuit 380 may extract a noise signal from the obtained biometric signal, and may analyze the magnitude of the extracted noise signal. The control circuit 380 may perform fast Fourier transform (FFT) on the digital signal which is converted from the biometric signal via the A/D converter 350, so as to analyze the magnitude of noise. When the gain of the feedback amplifier 370 is increased, a noise component included in the biometric signal may be offset due to a noise component feedback to the body of the user and thus, the magnitude of the noise may be reduced. The control circuit 380 may increase the gain of the feedback amplifier 370 and may analyze noise during a predetermined period of time, and may set an appropriate feedback gain.

If the gain of the feedback amplifier 370 is incrementally increased, the magnitude of noise decreases. However, if the gain is increased to be greater than or equal to a predetermined gain, the magnitude of noise may not be decreased, but rather increased. The control circuit 380 may obtain a biometric signal by increasing a feedback gain and may analyze the magnitude of noise, until the magnitude of noise becomes increased again. If the magnitude of noise is decreased, and then, becomes increased again, the control circuit 380 may set the gain of the feedback amplifier 370 to a feedback gain used immediately before the magnitude of noise is increased. The control circuit 380 may set the gain of the feedback amplifier 370, and may measure a biometric signal.

The control circuit 380 may analyze the magnitude of noise using at least two input signals (e.g., ADC1 and ADC2) output from the multiplexer 340. The control circuit 380 may perform FFT on two input signals and may analyze the magnitude of noise. The at least two input signals output from the multiplexer 340 may go through the A/D converter 350, and may be converted into a first digital signal and a second digital signal. The control circuit 380 may compare the magnitudes of noise of the first digital signal and the second digital signal. The control circuit 380 may control the output of the multiplexer 340 based on a result of the comparison. For example, if a difference in the magnitude of noise exceeds a reference value, the control circuit 380 may control the output of the multiplexer 340 so as to adjust the areas of the first electrode 310 and the second electrode 320. The adjusting of the areas of the first electrode 310 and the second electrode 320 may be adjusting the number of electrode nodes included in the first electrode 310 and the second electrode 320. For example, the control circuit 380 may adjust the areas of the first electrode 310 and the second electrode 320 by setting the output of the multiplexer 340 in the state in which the difference in the magnitude of noise is less than a reference value. The control circuit 380 may set an area, and may measure a biometric signal.

According to certain embodiments, the control circuit 380 may perform at least one method between a first method that reduces the magnitude of noise by adjusting the gain of the feedback amplifier 370 and a second method that reduces the magnitude of noise by controlling the output of the multiplexer 340. Alternatively, the control circuit 380 may perform the second method after performing the first method. The control circuit 380 may perform the first method, and may determine whether to perform the second method based on the magnitude of noise. The control circuit 380 may perform the second method if the magnitude of noise exceeds a predetermined noise threshold value, and may not perform the second method if the magnitude of noise is less than or equal to the noise threshold value. Alternatively, the control circuit 380 may perform the second method, and may determine whether to perform the first method based on the magnitude of noise. The control circuit 380 may perform the first method if the magnitude of noise exceeds a predetermined noise threshold value, and may not perform the first method if the magnitude of noise is less than or equal to the noise threshold value.

According to certain embodiments, in the case of measuring a biometric signal using an electrode, noise (or a noise signal) such as a power source noise or a motion artifact may be present. Alternatively, if a predetermined body part (e.g., a wrist, a finger, or the like) of a user that is in contact with an electrode is dry, or if the body of the user is not properly in contact with an electrode, this may act as an imbalance of a noise input and may affect measuring of a biometric signal. Particularly, an electronic device, such as a wearable device (e.g., FIG. 2A and FIG. 2B), is manufactured to be lightweight and small, and thus, the area of an electrode is limited and a contact impedance is increased, and noise is increased due to the instability of a posture for measurement. Accordingly, a signal to noise ratio (SNR) may be decreased. Alternatively, noise varies in real time according to surrounding environment. Accordingly, the electronic device automatically adjusts the value of a feedback gain so as to reduce a common noise, and may change the configuration of the area of an electrode so as to reduce a differential noise. Accordingly, the SNR of a biometric signal may be increased.

An electronic device (e.g., the electronic device 200 of FIGS. 2A and 2B) according to certain embodiments may include: a first electrode (e.g., the first electrode 310 of FIGS. 3A and 3B), a second electrode (e.g., the second electrode 320 of FIGS. 3A and 3B), and a third electrode (e.g., the third electrode 330 of FIGS. 3A and 3B) which are in contact with a body part of a user; an instrumentation amplifier (e.g., the instrumentation amplifier 360 of FIGS. 3A and 3B) which differentially amplifies signals received from the first electrode and the second electrode; a feedback amplifier (e.g., the feedback amplifier 370 of FIGS. 3A and 3B) which feeds back a feedback noise to a body part of the user via the third electrode; and a control circuit (e.g., the control circuit 380 of FIGS. 3A and 3B), and the control circuit is configured to analyze the magnitude of noise using a biometric signal obtained from the instrumentation amplifier, and to control the gain of the feedback amplifier based on a result of the analysis.

The control circuit may be configured to analyze the magnitude of noise included in the biometric signal by increasing the gain of the feedback amplifier.

If the magnitude of the noise included in the biometric signal is increased, the control circuit may be configured to suspend increasing the gain of the feedback amplifier, and to set the gain of the feedback amplifier to a feedback gain used before the magnitude of the noise is increased.

The electronic device may further include a multiplexer disposed between the first and second electrodes and the instrumentation amplifier, and configured to transfer outputs of the first electrode and the second electrode to the instrumentation amplifier.

The multiplexer may be configured to transfer all signals input from the first electrode and the second electrode to the instrumentation amplifier, or to transfer part of the signals input from the first electrode and the second electrode to the instrumentation amplifier.

The control circuit may be configured to analyze the magnitude of noise using at least two input signals output from the multiplexer, and to adjust the number of electrode nodes or the locations of the electrode nodes included in the first electrode and the second electrode based on a result of the analysis.

If a difference between noise signals included in the two input signals exceeds a reference value, the control circuit may be configured to control the output of the multiplexer so as to adjust an area of the first electrode and an area of the second electrode.

The control circuit may be configured to control the output of the multiplexer based on the magnitude of noise included in a biometric signal obtained after the gain of the feedback amplifier is set.

If the magnitude of the noise included in the biometric signal exceeds a predetermined noise threshold value, the control circuit may be configured to control the output of the multiplexer.

The first electrode may be disposed in a foreside of the electronic device, and the second electrode and the third electrode may be disposed in a rear side of the electronic device.

The first electrode and the third electrode may be disposed in a foreside of the electronic device, and the second electrode may be disposed in a rear side of the electronic device.

An electronic device (e.g., the electronic device 200 of FIGS. 2A and 2B) according to certain embodiments may include: a first electrode (e.g., the first electrode 310 of FIGS. 3A and 3B), a second electrode (e.g., the second electrode 320 of FIGS. 3A and 3B), and a third electrode (e.g., the third electrode 330 of FIGS. 3A and 3B) which are in contact with a body part of a user; a multiplexer (e.g., the multiplexer 340 of FIGS. 3A and 3B) connected to the first electrode and the second electrode in parallel; an instrumentation amplifier (e.g., the instrumentation amplifier 360 of FIGS. 3A and 3B) which differentially amplifies a signal output from the multiplexer; a feedback amplifier (e.g., the feedback amplifier 370 of FIGS. 3A and 3B) which feeds back a feedback noise to a body part of the user via the third electrode; and a control circuit (e.g., the control circuit 380 of FIGS. 3A and 3B), wherein the control circuit is configured to analyze the magnitude of noise using the signal output from the multiplexer, and to adjust the area of the first electrode and the area of the second electrode based on a result of the analysis.

The control circuit is configured to analyze the magnitude of noise using at least two input signals output from the multiplexer, and may control the output of the multiplexer based on a result of the analysis.

The control circuit is configured to control the output of the multiplexer so as to adjust the areas of the first electrode and the second electrode if the difference between noise signals included in the two input signals exceeds a reference value.

The control circuit may be configured to adjust the gain of the feedback amplifier if the magnitude of noise included in a biometric signal obtained from the instrumentation amplifier exceeds a predetermined noise threshold value after the area of the electrode is adjusted.

FIG. 4 is a flowchart 400 illustrating a method of measuring a biometric signal using an electrode by an electronic device according to certain embodiments.

Referring to FIG. 4, in operation 401, the control circuit 380 (e.g., the processor 120 of FIG. 1) of an electronic device (e.g., the electronic device 101 of FIG. 1 or the electronic device 200 of FIGS. 2A and 2B) according to certain embodiments may analyze a first noise magnitude from a first biometric signal. The first biometric signal may be input to the control circuit 380 via an electrode (e.g., the first electrode 310 and the second electrode 320 of FIGS. 3A and 3B), a multiplexer (e.g., the multiplexer 340 of FIGS. 3A and 3B), and an instrumentation amplifier (e.g., the instrumentation amplifier 360 of FIGS. 3A and 3B). For example, the control circuit 380 may extract a first noise signal from the first biometric signal and may analyze the magnitude of the extracted first noise signal. For example, a digital signal converted from the biometric signal via the A/D converter 350 may be converted into a signal having a frequency characteristic via FFT. The control circuit 380 may analyze the magnitude of noise using the signal having the frequency characteristic. For example, the signal having the frequency characteristic shows a peak at a predetermined frequency (e.g., 50 to 60 Hz), and the peak point may be extracted as a noise signal.

In operation 403, the control circuit 380 may increase a feedback gain (or a gain value). The feedback gain may be the gain of the feedback amplifier (e.g., the feedback amplifier 370 of FIGS. 3A and 3B). The control circuit 380 may increase the gain of the feedback amplifier 370. The magnitude of a noise signal (or component) feedback to the body of a user may be changed if the gain of the feedback amplifier 370 is increased.

In operation 405, the control circuit 380 may analyze a second noise magnitude from a second biometric signal. The first biometric signal may be a biometric signal obtained before the feedback gain is increased, and the second biometric signal may be a biometric signal obtained after the feedback gain is increased. The control circuit 380 may extract a second noise signal from the second biometric signal, and may analyze the magnitude of the extracted second noise signal. If the gain of the feedback amplifier 370 is increased, a noise component included in the biometric signal may be removed due to a noise component feedback to the body of the user and thus, the magnitude of the noise may be reduced. For example, a noise signal may be feedback to the body of the user via the third electrode 330, and a biometric signal may be input to a positive input and a negative input of the instrumentation amplifier 360 via the first electrode 310 and the second electrode 320. If the noise signal feedback to the body of the user is input to a positive input and a negative input, and goes through the instrumentation amplifier 360, the noise signal may be removed. However, a noise signal that passes through the instrumentation amplifier 360 is not removed via offset, but is rather increased if the gain become greater than or equal to a predetermined gain.

In operation 407, the control circuit 380 may determine whether noise is increased. The control circuit 380 may compare the magnitude of noise analyzed in operation 401 and the magnitude of noise analyzed in operation 405, and may determine whether noise is increased. If noise is increased, the control circuit 380 proceeds with operation 409. If noise is not increased, the control circuit 380 returns to operation 403. The control circuit 380 repeatedly performs operations 403 and 405, and may analyze the magnitude of noise by increasing a feedback gain until the magnitude of noise becomes increased after being decreased.

If noise is increased, the control circuit 380 may set a feedback gain in operation 409. If the feedback gain is increased, noise is decreased and then, noise may become increased again at a predetermined point in time. For example, the control circuit 380 may set the gain of the feedback amplifier 370 to a feedback gain used immediately before the magnitude of noise is increased.

In operation 411, the control circuit 380 may measure a biometric signal. The control circuit 380 sets a gain of the feedback amplifier 370 which makes the magnitude of noise to be decreased (or removed), and may measure (or produce) a biometric signal using a signal received via the first electrode 310 and the second electrode 320, the multiplexer 340, and the instrumentation amplifier 360. The control circuit 380 may produce at least one piece of biometric information among ECG, GSR, EEG, or BIA, using the measured biometric signal. The control circuit 380 may store biometric information in a memory (e.g., the memory 130 of FIG. 1), or may provide the same to a user via a display (e.g., the display device 160 of FIG. 1). According to certain embodiments, the control circuit 380 may perform operations in the flowchart of FIG. 7 after performing operation 409.

Figure 5A:
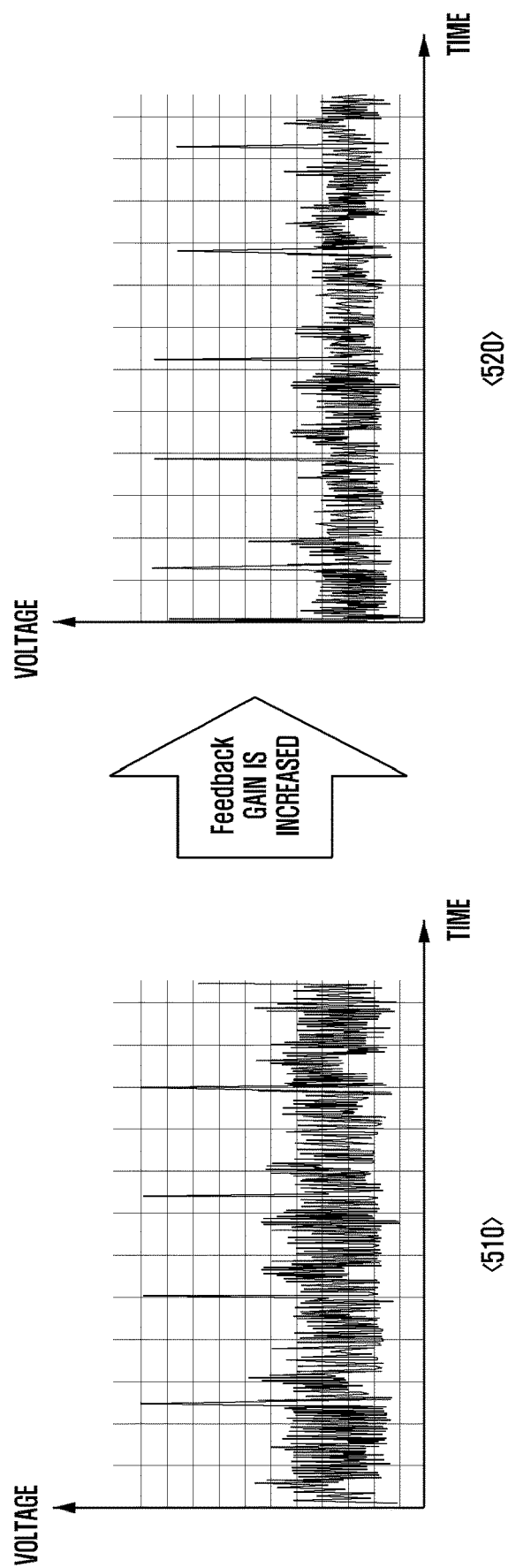
FIGS. 5A and 5B are diagrams illustrating characteristics of a noise signal included in a biometric signal according to certain embodiments.
Figure 5B:
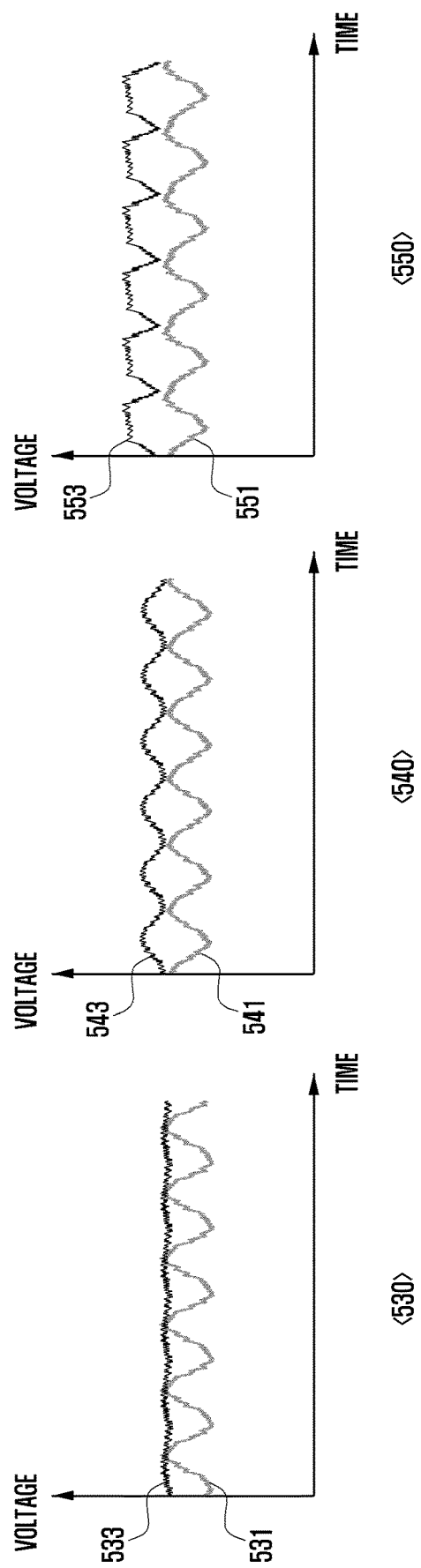

FIGS. 5A and 5B are diagrams illustrating characteristics of a noise signal included in a biometric signal according to certain embodiments.

FIG. 5A is a diagram illustrating a noise signal when the gain of a feedback amplifier (e.g., the feedback amplifier 370 of FIGS. 3A and 3B) is increased.

Referring to FIG. 5A, a first noise signal graph 510 shows a noise signal extracted from a biometric signal before the gain of the feedback amplifier 370 is increased. A second noise signal graph 520 shows a noise signal extracted from a biometric signal after the gain of the feedback amplifier 370 is increased. By comparing the first noise signal graph 510 and the second noise signal graph 520, it is recognized that the magnitude of noise is decreased if the gain of the feedback amplifier 370 is increased.

FIG. 5B is a diagram illustrating the relationship between the gain of the feedback amplifier 370 and a noise signal.

Referring to FIG. 5B, a first signal relationship graph 530 shows a first power source noise signal 531 and a first noise signal 533 extracted from a first biometric signal when the feedback amplifier 370 is set to a first gain. The first power source noise signal 531 may be noise produced by a current provided to an electrode (e.g., the first electrode 310 and the second electrode 320 of FIGS. 3A and 3B). The magnitude of the first power source noise signal 531 may be smaller than the magnitude of the first noise signal 533 and thus, the first power source noise signal 531 may not be offset. Therefore, an electronic device (e.g., the electronic device 101 of FIG. 1 or the electronic device 200 of FIGS. 2A and 2B) needs to remove the first noise signal from the first biometric signal in order to obtain a biometric signal.

A second signal relationship graph 540 shows a second power source noise signal 541 and a second noise signal 543 extracted from a second biometric signal when the feedback amplifier 370 is set to a second gain which is higher than the first gain. The magnitude of the second power source noise signal 541 may be similar to the magnitude of the second noise signal 543 and thus, part of the second noise signal 543 may be offset and may be removed. Therefore, the electronic device 200 may obtain a biometric signal by removing the remaining part of the second noise signal which is not removed from the second biometric signal.

A third signal relationship graph 550 shows a third power source noise signal 551 and a third noise signal 553 extracted from a third biometric signal when the feedback amplifier 370 is set to a third gain which is higher than the second gain. Part of the third noise signal 553 is removed due to saturation and thus, the third power source noise signal 551 may not be offset. For example, the shape of the third power noise signal 551 and the shape of the third noise signal 553 do not match and thus, they may not be offset. Therefore, the electronic device 200 may need to remove the third noise signal from the third biometric signal, in order to obtain a biometric signal.

Referring to FIGS. 5A and 5B, if the gain of the feedback amplifier 370 is increased, a noise component included in a biometric signal may be offset due to a noise component feedback to the body of the user and thus, the magnitude of noise may be reduced. However, referring to the second signal relationship graph 540 and the third signal relationship graph 550, if the gain of the feedback amplifier 370 exceeds a threshold value, a noise component feedback to the body of the user is greater than a noise component included in a biometric signal and thus, the noise components are not offset against each other and may be increased. According to the embodiments, by setting the gain of the feedback amplifier 370 to a feedback gain used immediately before the magnitude of noise is increased, noise components are offset against each other and removed.

Figure 6A:
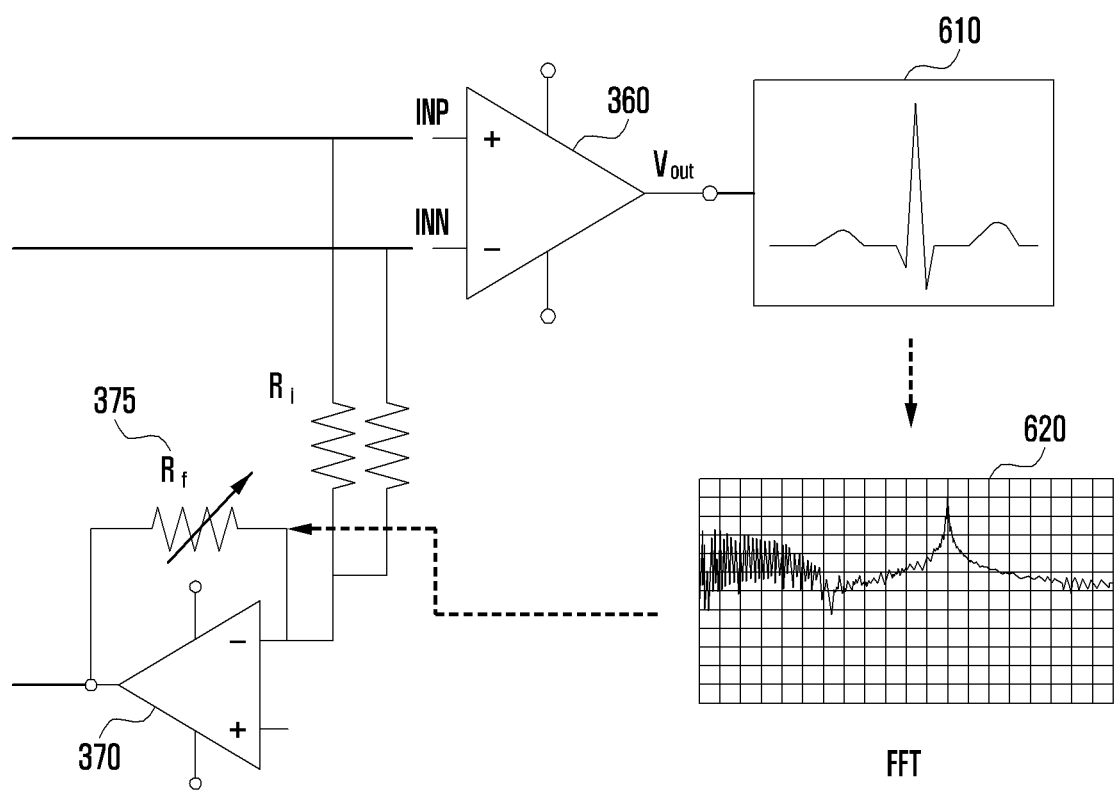
FIGS. 6A and 6B are diagrams illustrating a change in a noise signal according to an adjustment of a feedback gain according to certain embodiments.
Figure 6B:
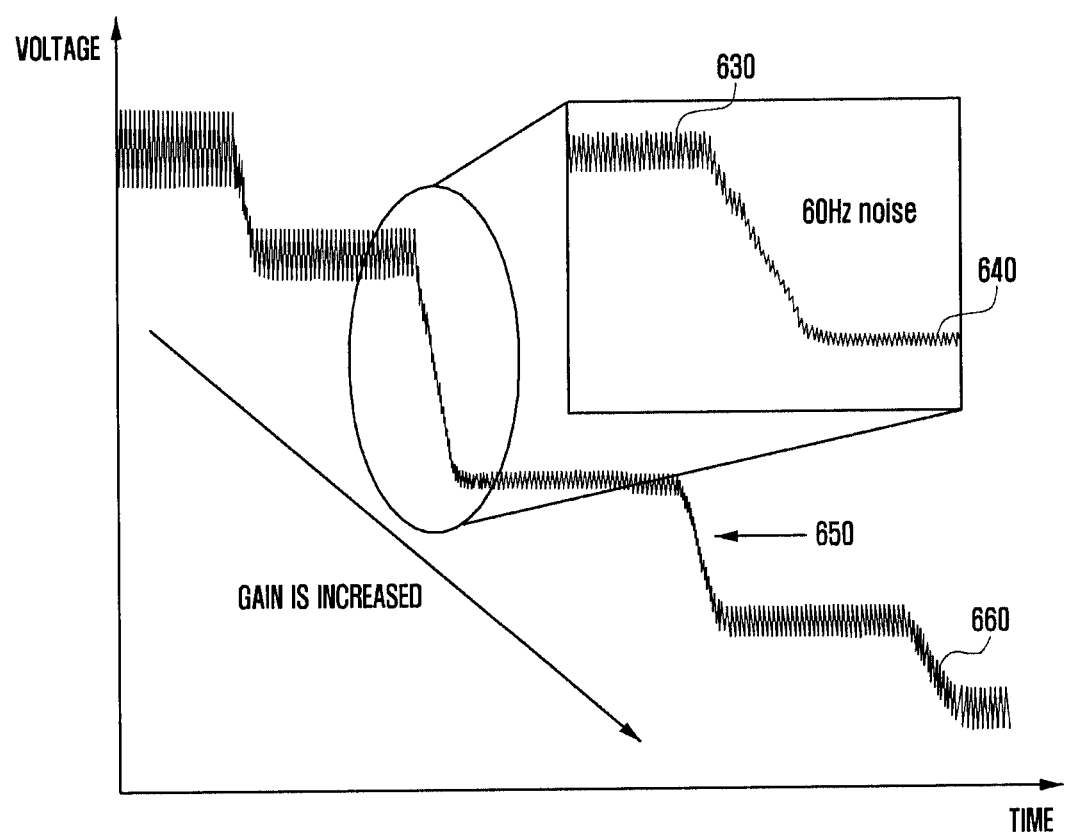

FIGS. 6A and 6B are diagrams illustrating a change in a noise signal according to adjustment of a feedback gain according to certain embodiments.

Referring to FIG. 6A, a control circuit (e.g., the processor 120 of FIG. 1, and the control circuit 380 of FIGS. 3A and 3B) of an electronic device (e.g., the electronic device 101 of FIG. 1 and the electronic device 200 of FIGS. 2A and 2B) according to certain embodiments may adjust a gain 375 (Rf) of the feedback amplifier 370 using a biometric signal 610 obtained from the instrumentation amplifier 360. For example, the control circuit 380 may analyze a noise signal by performing fast Fourier transform (FFT) 620 on the biometric signal 610. The noise signal analyzed by performing the FFT 620 may be a power source noise component. The magnitude of an initial original noise signal that flows in through an electrode (e.g., the first electrode 310 and the second electrode 320 of FIG. 3A and FIG. 3B) may differ depending on a surrounding environment. The control circuit 380 may feed back, to the body of a user via the feedback amplifier 370, a noise signal extracted from the biometric signal 610 by increasing the gain 375 of the feedback amplifier 370. When the noise signal feedback to the body of the user via the third electrode 330 is input into a positive input (INP, +) and a negative input (INN, −) of the instrumentation amplifier 360 via the first electrode 310 and the second electrode 320, and passes through the instrumentation amplifier 360, the noise signal may be removed.

Referring to FIG. 6B, if the gain 375 of the feedback amplifier 370 is increased, the magnitude of a noise signal included in a biometric signal obtained from the instrumentation amplifier 360 may be decreased. A first noise signal 630 indicates the magnitude of a noise signal included in a biometric signal before the gain 375 of the feedback amplifier 370 is increased. A second noise signal 640 indicates the magnitude of a noise signal included in a biometric signal after the gain 375 of the feedback amplifier 370 is increased. However, if the gain 375 of the feedback amplifier 370 is continuously increased, the magnitude of a noise signal may become increased again due to saturation 650. If the gain 375 of the feedback amplifier 370 is continuously increased even after the second noise signal 640, the magnitude of a third noise signal 660 is increased due to saturation 650.

Figure 7:
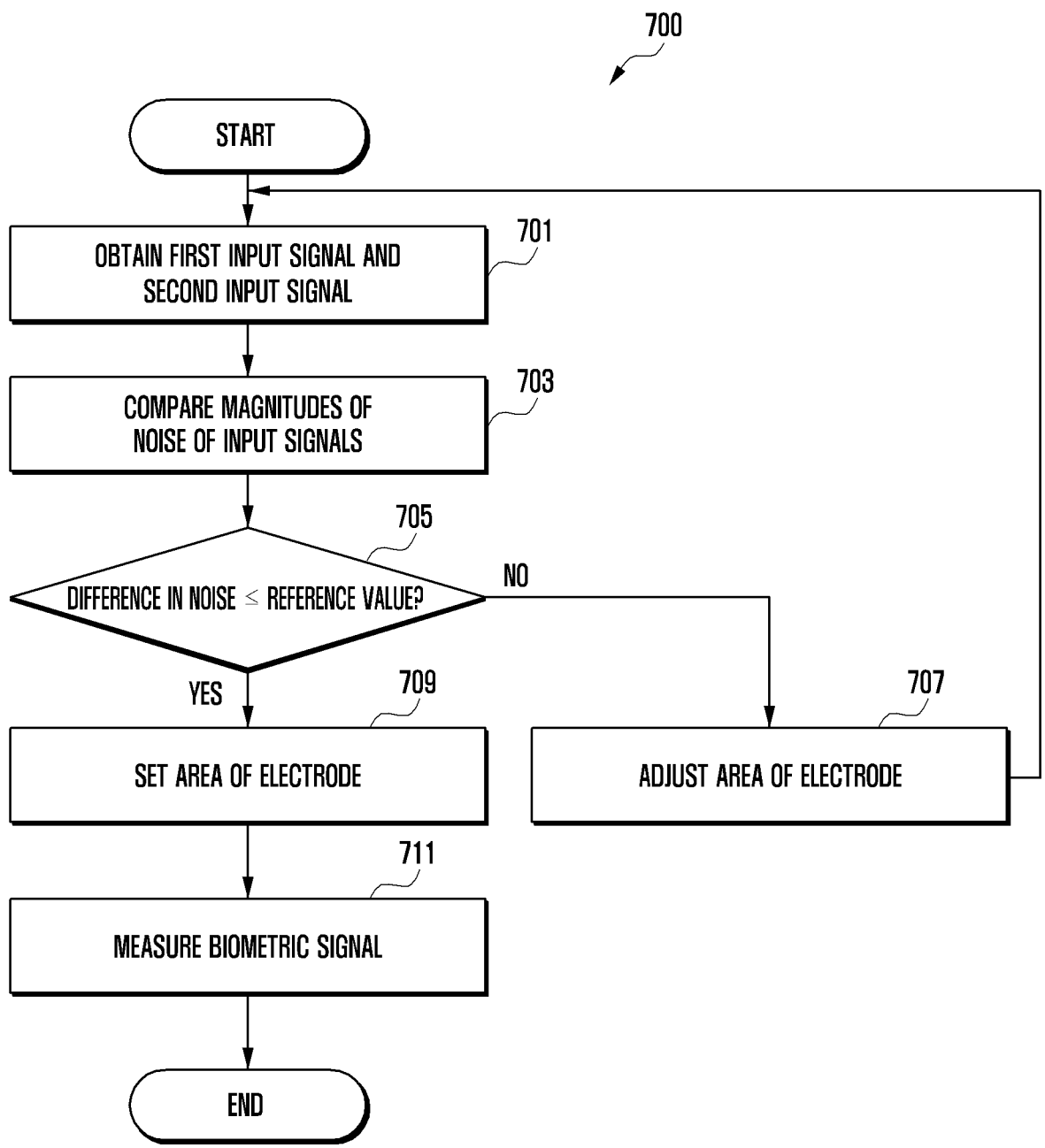
FIG. 7 is a flowchart 700 illustrating a method of measuring a biometric signal by adjusting the area of an electrode by an electronic device according to certain embodiments.

FIG. 7 is a flowchart 700 illustrating a method of measuring a biometric signal by adjusting the area of an electrode by an electronic device according to certain embodiments.

Referring to FIG. 7, in operation 701, the control circuit 380 (e.g., the processor 120 of FIG. 1) of an electronic device (e.g., the electronic device 101 of FIG. 1 or the electronic device 200 of FIGS. 2A and 2B) according to certain embodiments may obtain a first input signal and a second input signal. The first input signal and the second input signal may be signals output from a multiplexer (e.g., the multiplexer 340 of FIGS. 3A and 3B). For example, the first input signal is received via a first electrode (e.g., the first electrode 310 of FIG. 3A and FIG. 3B), and the second input signal is received via a second electrode (e.g., the second electrode 320 of FIGS. 3A and 3B).

In operation 703, the control circuit 380 may compare the magnitudes of noise of input signals. The first input signal and the second input signal output from the multiplexer 340 may go through the A/D converter 350, and may be converted into digital signals. The control circuit 380 may compare the magnitudes of noise of the digital signals converted from the first input signal and the second input signal. The control circuit 380 may respectively perform fast Fourier transform (FFT) on the digital signals converted from the first input signal and the second input signal, and may analyze a difference in noise. The control circuit 380 may extract a first noise signal by performing FFT on the first input signal and may extract a second noise signal by performing FFT on the second input signal. The control circuit 380 may compare the magnitude of the first noise signal and the magnitude of the second noise signal.

In operation 705, the control circuit 380 may determine whether the difference in noise is less than or equal to a reference value. In the case in which the magnitude of the first noise signal and the magnitude of the second noise signal are equal, the first noise signal and the second noise signal may be offset against each other when the first nose signal and the second noise signal pass through the instrumentation amplifier (e.g., the instrumentation amplifier 360 of FIGS. 3A and 3B), and the noise signals may be removed. However, if the difference in magnitude between the first noise signal and the second noise signal is large, the first noise signal and the second noise signal may not be offset against each other even though the first noise signal and the second noise signal pass through the instrumentation amplifier 360. In this instance, even though the noise signals pass through the instrumentation amplifier 360, a noise signal may be included in a biometric signal. The control circuit 380 may proceed with operation 707 if the difference in noise exceeds a reference value, and the control circuit 380 may proceed with operation 709 if the difference in noise is less than or equal to the reference value.

If the difference in noise exceeds the reference value, the control circuit 380 may adjust the area of an electrode in operation 707. If the first electrode 310 and the second electrode 320 are provided in the forms of matrices, the control circuit 380 may control the output of the multiplexer 340 so as to adjust the area of the electrode. For example, if the first electrode 310 and the second electrode 320 are provided in the forms of 3×3 matrices, and operations 701 to 705 are performed, only a biometric signal measured by a 2×2 matrix may be output as an output of the multiplexer 340. The control circuit 380 may perform control so that the first electrode 310 and the second electrode 320 output all input values of the 3×3 matrices as an output of the multiplexer 340. Alternatively, the control circuit 380 may perform control so that the first electrode 310 and the second electrode 320 output only a biometric signal measured by a 1×2 matrix as an output of the multiplexer 340. The control circuit 380 may perform operation 707, and may return to operation 701 so as to perform operations 701 to 705.

If the difference in noise is less than or equal to a reference value, the control circuit 380 may set the area of the electrode (e.g., the first electrode 310 and the second electrode 320) in operation 709. In the case in which the difference in noise is less than or equal to the reference value, if a biometric signal received via the electrode passes through the instrumentation amplifier 360, noise may be removed. The control circuit 380 may fix the area of the electrode which is used for measuring the current biometric signal. The control circuit 380 may fix (or set) the output of the multiplexer 340 used for measuring the current biometric signal.

In operation 711, the control circuit 380 may measure a biometric signal. The control circuit 380 may measure (or produce) a biometric signal using a signal received via the first electrode 310 and the second electrode 320 having areas which reduce (or remove) the magnitudes of noise, the multiplexer 340, and the instrumentation amplifier 360. The control circuit 380 may produce at least one piece of biometric information among ECG, GSR, EEG, or BIA, using the measured biometric signal. The control circuit 380 may store the biometric information in a memory (e.g., the memory 130 of FIG. 1), or may provide the same to a user via a display (e.g., the display device 160 of FIG. 1). According to certain embodiments, the control circuit 380 may selectively perform operations in the flowchart of FIG. 4 after performing operation 711.

Figure 8A:
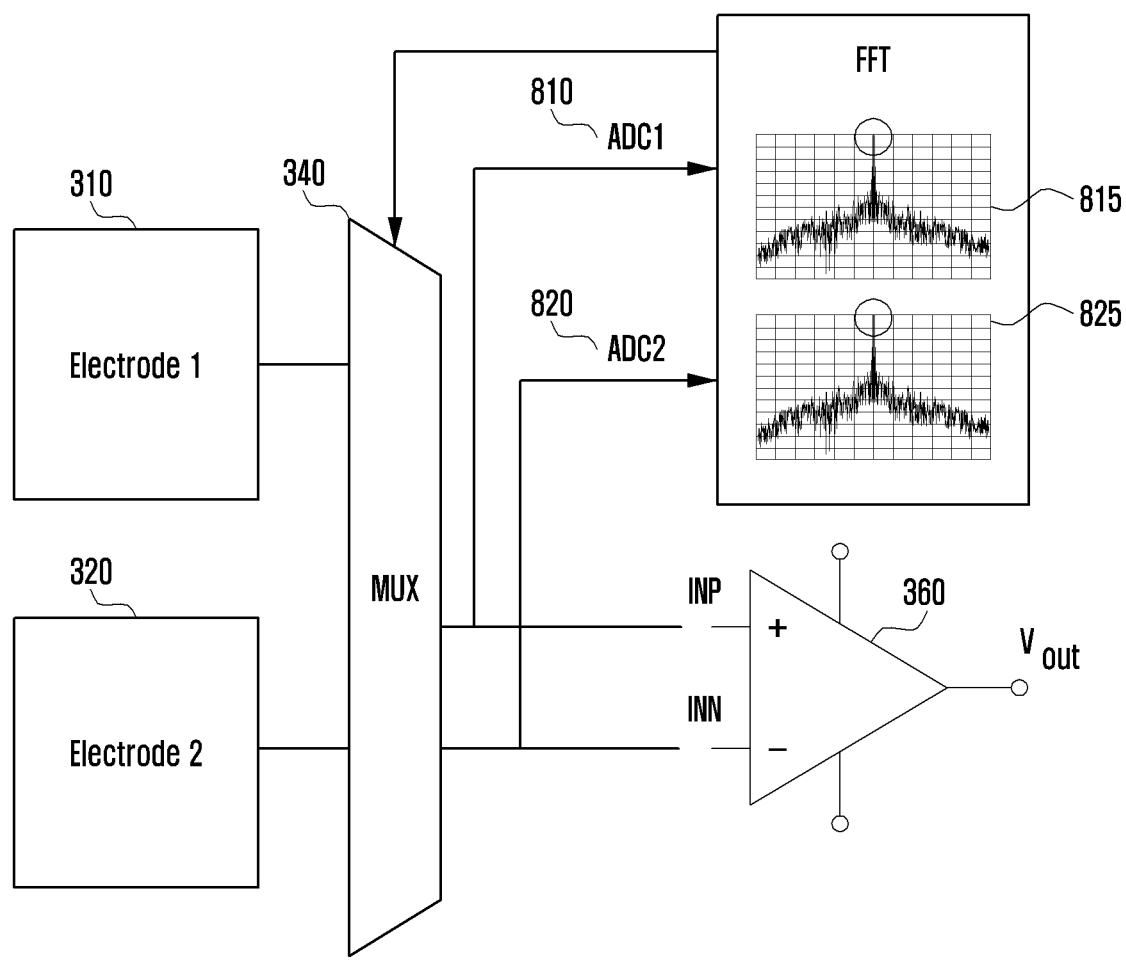
FIGS. 8A and 8B are diagrams illustrating an example of adjusting the area of an electrode according to the magnitude of noise according to certain embodiments.
Figure 8B:
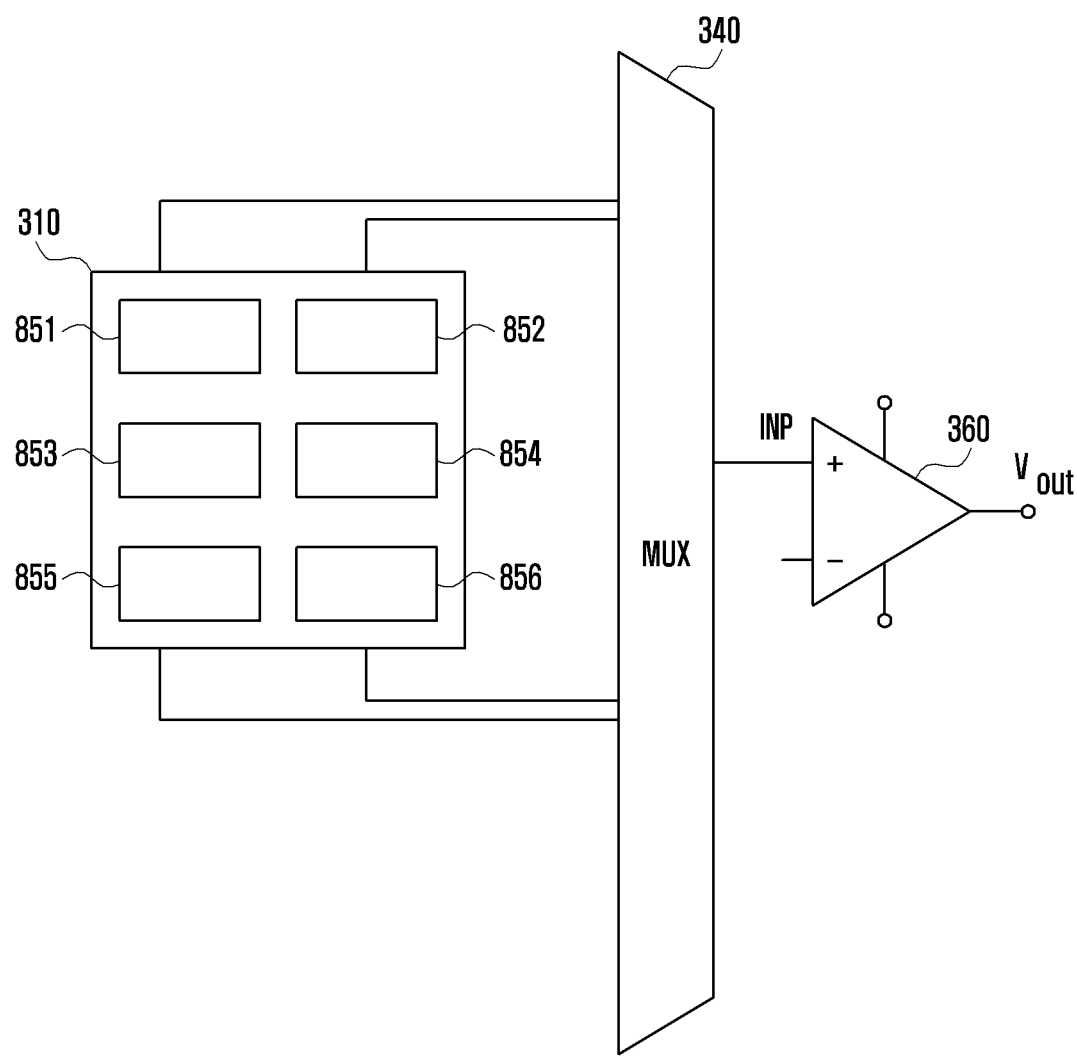

FIGS. 8A and 8B are diagrams illustrating an example of adjusting the area of an electrode according to the magnitude of noise according to certain embodiments.

FIG. 8A is a diagram illustrating an example of analyzing the magnitude of noise using an input signal.

Referring to FIG. 8A, the control circuit 380 (e.g., the processor 120 of FIG. 1) of an electronic device (e.g., the electronic device 101 of FIG. 1 or the electronic device 200 of FIGS. 2A and 2B) according to certain embodiments may analyze a difference in noise between a first input signal 810 (ADC1) and a second input signal 820 (ADC2). The first input signal 810 may be a signal that is received by the first electrode 310 and is output from the multiplexer 340. The second input signal 820 may be a signal that is received by the second electrode 320 and is output from the multiplexer 340. The control circuit 380 may convert the first input signal 810 and the second input signal 820 into digital signals, and may perform fast Fourier transform (FFT) on the digital signals. If FFT is performed on the digital signals converted from the first input signal 810 and the second input signal 820, the digital signals may be converted into signals having a frequency characteristic. A first frequency signal 815 may be converted from the first input signal 810 and a second frequency signal 825 may be converted from the second input signal 820. Each of the first frequency signal 815 and the second frequency signal 825 shows a peak at a predetermined frequency (e.g., 50 to 60 Hz), and the peak point may be extracted as a noise signal. The control circuit 380 may compare the magnitudes of noise of the first frequency signal 815 and the second frequency signal 825.

FIG. 8B is a diagram illustrating an example of adjusting the area of an electrode.

Referring to FIG. 8B, an electrode (e.g., the first electrode 310 of FIGS. 3A and 3B) may be provided in the form of a 2×3 matrix. Although the first electrode 310 is illustrated in the drawing, the electrode may be the second electrode 320 of FIGS. 3A and 3B. For example, the first electrode 310 may include a first electrode node 851, a second electrode 852, a third electrode node 853, a fourth electrode node 854, a fifth electrode node 855, and a sixth electrode node 856. Each of the first electrode node 851 to the sixth electrode node 856 may be connected to an input node of the multiplexer 340. The multiplexer 340 may adjust the number (or the area) of the electrode nodes or the locations of the electrode nodes included in the first electrode 310, as controlled by a control circuit (e.g., the control circuit 380 of FIGS. 3A and 3B). The control circuit 380 may control the output of the multiplexer 340 based on the magnitude of noise or the magnitude of a contact impedance.

According to certain embodiments, the multiplexer 340 may adjust the area of the first electrode 310. The multiplexer 340 may transfer only the outputs of the first electrode node 851 and the second electrode node 852 to the instrumentation amplifier 360. The multiplexer 340 may transfer only the outputs of the third electrode node 853 and the fourth electrode node 854 to the instrumentation amplifier 360. The multiplexer 340 may transfer only the outputs of the fifth electrode node 855 and the sixth electrode node 856 to the instrumentation amplifier 360. The multiplexer 340 may transfer only the outputs of the first electrode node 851 to the fourth electrode node 854 to the instrumentation amplifier 360. The multiplexer 340 may transfer only the outputs of the third electrode node 853 to the sixth electrode node 856 to the instrumentation amplifier 360.

According to certain embodiments, the multiplexer 340 may perform control so that only signals measured by some of a plurality of electrode nodes included in the first electrode 310 are used as a biometric signal. For example, the control circuit 380 may measure a biometric signal using signals obtained from left electrode nodes according to the state of user skin. The multiplexer 340 may transfer only the outputs of the first electrode node 851, the third electrode node 853, and the fifth electrode 855 to the instrumentation amplifier 360. Alternatively, the control circuit 380 may measure a biometric signal using signals obtained from right electrode nodes according to the state of user skin. The multiplexer 340 may transfer only the outputs of the second electrode node 852, the fourth electrode node 854, and the sixth electrode 856 to the instrumentation amplifier 360.

Figure 9:
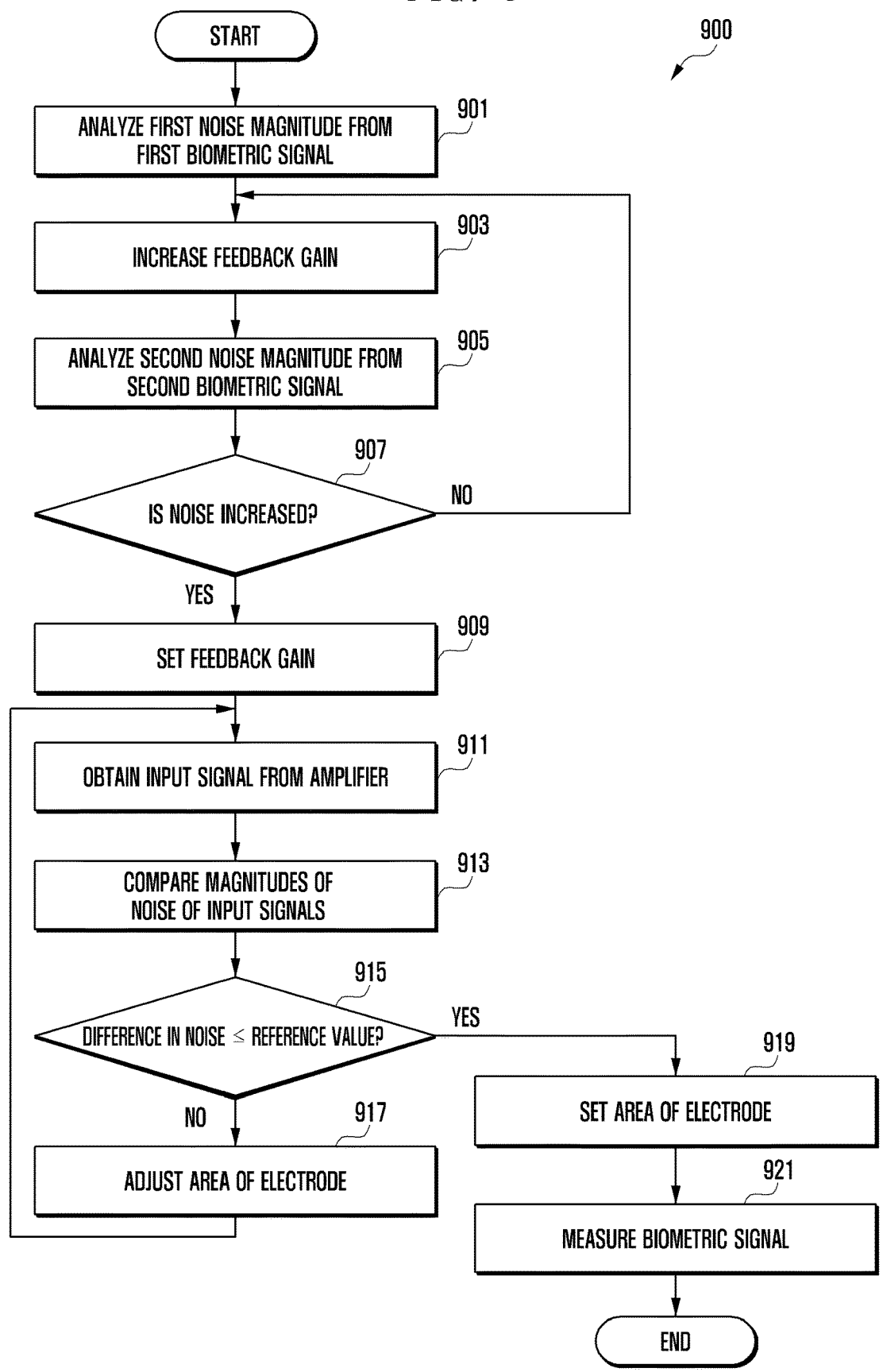
FIG. 9 is a flowchart 900 illustrating a method of measuring a biometric signal by reducing the magnitude of noise by an electronic device according to certain embodiments.

FIG. 9 is a flowchart 900 illustrating a method of measuring a biometric signal by reducing the magnitude of noise by an electronic device according to certain embodiments.

Referring to FIG. 9, in operation 901, the control circuit 380 (e.g., the processor 120 of FIG. 1) of an electronic device (e.g., the electronic device 101 of FIG. 1 or the electronic device 200 of FIGS. 2A and 2B) according to certain embodiments may analyze a first noise magnitude from a first biometric signal. The first biometric signal may be input to the control circuit 380 via an electrode (e.g., the first electrode 310 and the second electrode 320 of FIGS. 3A and 3B), a multiplexer (e.g., the multiplexer 340 of FIGS. 3A and 3B), and an instrumentation amplifier (e.g., the instrumentation amplifier 360 of FIGS. 3A and 3B). The control circuit 380 may extract a first noise signal from the first biometric signal, and may analyze the magnitude of the extracted first noise signal. Operation 901 is the same as, or similar to, operation 401 of FIG. 4, and thus, detailed descriptions thereof will be omitted.

In operation 903, the control circuit 380 may increase a feedback gain (or a gain value). The feedback gain may be a degree by which a signal of a feedback amplifier (e.g., the feedback amplifier 370 of FIG. 3A and FIG. 3B) is amplified. The control circuit 380 may increase the gain of the feedback amplifier 370. The magnitude of a noise signal (or component) feedback to the body of a user may be changed if the gain of the feedback amplifier 370 is increased. Operation 903 is the same as, or similar to, operation 403 of FIG. 4, and thus, detailed descriptions thereof will be omitted.

In operation 905, the control circuit 380 may analyze a second noise magnitude from a second biometric signal. The first biometric signal may be a biometric signal used before the feedback gain is increased, and the second biometric signal may be a biometric signal used after the feedback gain is increased. The control circuit 380 may extract a second noise signal from the second biometric signal, and may analyze the magnitude of the extracted second noise signal. Operation 905 is the same as, or similar to, operation 405 of FIG. 4, and thus, detailed descriptions thereof will be omitted.

In operation 907, the control circuit 380 may determine whether noise is increased. The control circuit 380 may compare the magnitude of noise analyzed in operation 901 and the magnitude of noise analyzed in operation 905, and may determine whether noise is increased. If noise is increased, the control circuit 380 proceeds with operation 909. If noise is not increased, the control circuit 380 returns to operation 903. Operation 907 is the same as, or similar to, operation 407 of FIG. 4, and thus, detailed descriptions thereof will be omitted.

If noise is increased, the control circuit 380 may set a feedback gain in operation 909. If the feedback gain is increased, noise is decreased and then, noise may become increased again at a predetermined point in time. For example, the control circuit 380 may set the gain of the feedback amplifier 370 to a feedback gain used immediately before the magnitude of noise becomes increased.

In operation 911, the control circuit 380 may obtain an input signal from the amplifier (e.g., the instrumentation amplifier 360 of FIGS. 3A and 3B). The input signal may include a first input signal and a second input signal output from the multiplexer (e.g., the multiplexer 340 of FIGS. 3A and 3B). For example, the first input signal is received via a first electrode (e.g., the first electrode 310 of FIGS. 3A and 3B), and the second input signal is received via a second electrode (e.g., the second electrode 320 of FIGS. 3A and 3B). Operation 911 is the same as, or similar to, operation 701 of FIG. 7, and thus, detailed descriptions thereof will be omitted.

In operation 913, the control circuit 380 may compare the magnitudes of noise of the input signals. The input signals (e.g., the first input signal and the second input signal) may pass through an A/D converter (e.g., the A/D converter 350 of FIGS. 3A and 3B) and may be converted into digital signals. The control circuit 380 may respectively perform fast Fourier transform on the digital signals converted from the first input signal and the second input signal, and may analyze a difference in noise. For example, the control circuit 380 may extract a first noise signal by performing FFT on the first input signal, and may extract a second noise signal by performing FFT on the second input signal. The control circuit 380 may compare the magnitude of the first noise signal and the magnitude of the second noise signal. Operation 913 is the same as, or similar to, operation 703 of FIG. 7, and thus, detailed descriptions thereof will be omitted.

In operation 915, the control circuit 380 may determine whether the difference in noise is less than or equal to a reference value. In the case in which the magnitude of the first noise signal and the magnitude of the second noise signal are equal, the first noise signal and the second noise signal may be offset against each other if the first noise signal and the second noise signal pass through the instrumentation amplifier 360, and the noise signals may be removed. However, if the difference in magnitude between the first noise signal and the second noise signal is large, the first noise signal and the second noise signal may not be offset against each other even though the first noise signal and the second noise signal pass through the instrumentation amplifier 360. The control circuit 380 may proceed with operation 917 if the difference in noise exceeds the reference value, and the control circuit 380 may proceed with operation 919 if the difference in noise is less than or equal to the reference value. Operation 915 is the same as, or similar to, operation 705 of FIG. 7, and thus, detailed descriptions thereof will be omitted.

If the difference in noise exceeds the reference value, the control circuit 380 may adjust the area of the electrode in operation 917. If the first electrode 310 and the second electrode 320 are provided in the forms of matrices, the control circuit 380 may control the output of the multiplexer 340 so as to adjust the area of the electrode. For example, if the first electrode 310 and the second electrode 320 are provided in the forms of 2×3 matrices as shown in FIG. 8B, and operations 911 to 915 are performed, only a biometric signal measured by a 2×2 matrix (e.g., the first electrode node 851 to the fourth electrode node 854) may be output as an output of the multiplexer 340. The control circuit 380 may perform control so that the first electrode 310 and the second electrode 320 output all input values of the 2×3 matrices (e.g., the first electrode node 851 to the sixth electrode node 856) as an output of the multiplexer 340. Alternatively, the control circuit 380 may perform control so that the first electrode 310 and the second electrode 320 output only a biometric signal measured by the first electrode node 851 and the second electrode node 852 as an output of the multiplexer 340. The control circuit 380 may perform operation 917, and may return to operation 911 so as to perform operations 911 to 915. Operation 917 is the same as, or similar to, operation 707 of FIG. 7, and thus, detailed descriptions thereof will be omitted.

If the difference in noise is less than or equal to a reference value, the control circuit 380 may set the area of the electrode (e.g., the first electrode 310 and the second electrode 320) in operation 919. In the case in which the difference in noise is less than or equal to the reference value, if a biometric signal received via the electrode passes through the instrumentation amplifier 360, noise may be removed. The control circuit 380 may fix the area of the electrode used for measuring the current biometric signal. The control circuit 380 may fix (or set) the output of the multiplexer 340 which is set when performing operation 911. Operation 919 is the same as, or similar to, operation 709 of FIG. 7, and thus, detailed descriptions thereof will be omitted.

In operation 921, the control circuit 380 may measure a biometric signal. The control circuit 380 may measure (or produce) a biometric signal using a signal received via the first electrode 310 and the second electrode 320, the multiplexer 340, and the instrumentation amplifier 360. The control circuit 380 may produce at least one piece of biometric information among ECG, GSR, EEG, or BIA, using the measured biometric signal. The control circuit 380 may store the biometric information in a memory (e.g., the memory 130 of FIG. 1), or may provide the same to a user via a display (e.g., the display device 160 of FIG. 1). Operation 921 is the same as, or similar to, operation 711 of FIG. 7, and thus, detailed descriptions thereof will be omitted.

Figure 10A:
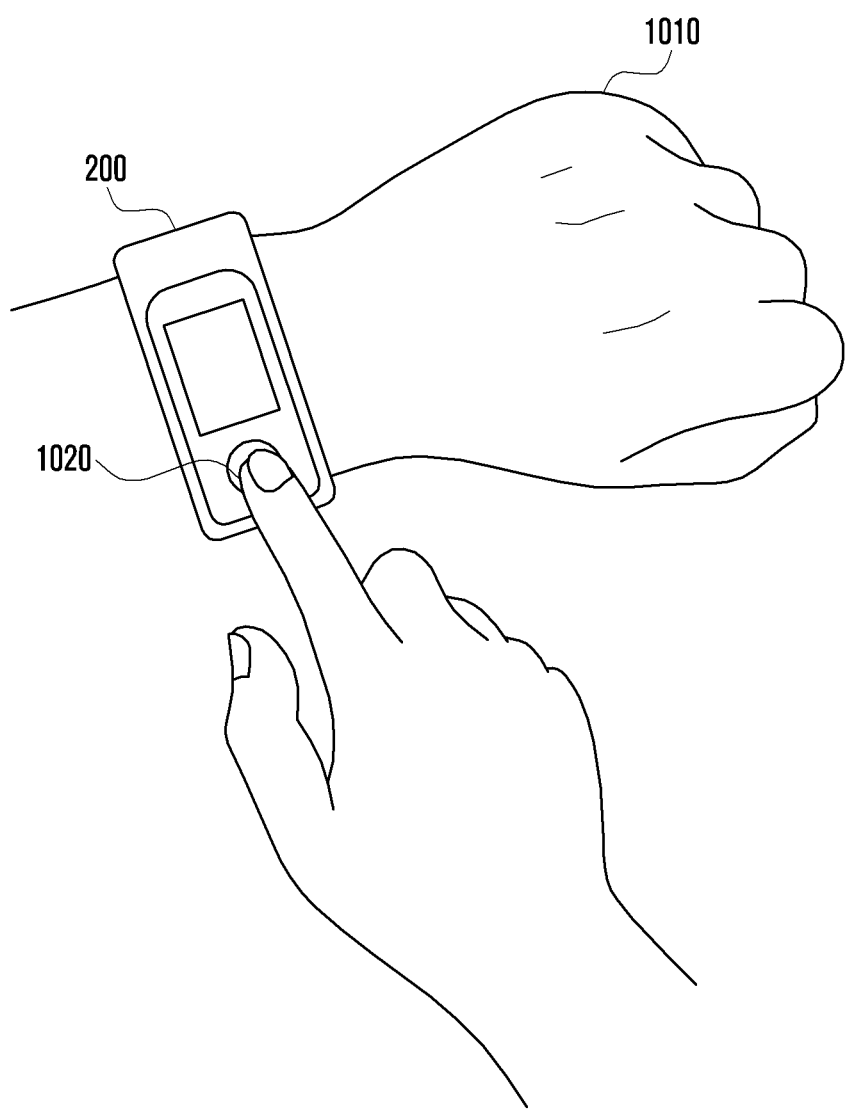
FIGS. 10A and 10B are diagrams illustrating an example of measuring a biometric signal using an electrode according to certain embodiments.
Figure 10B:
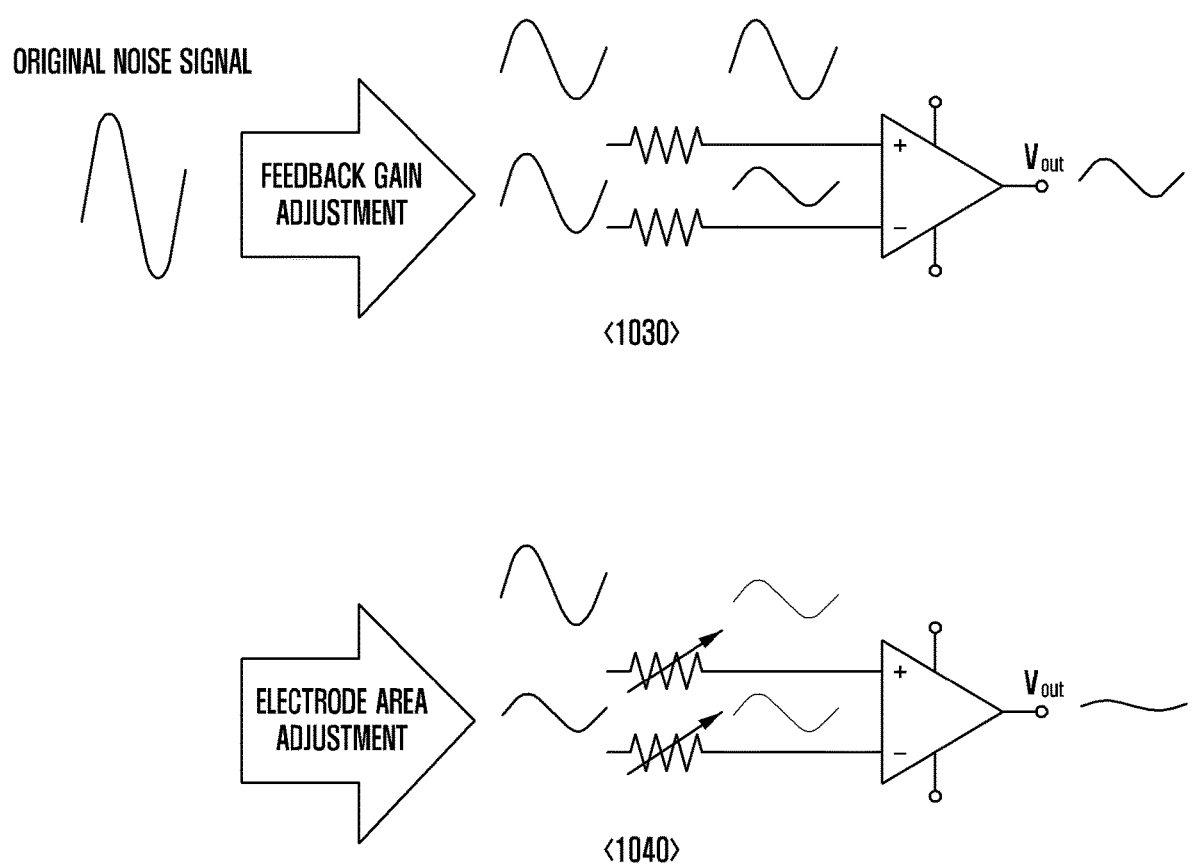

FIGS. 10A and 10B are diagrams illustrating an example of measuring a biometric signal using an electrode according to certain embodiments.

FIG. 10A is a diagram illustrating an example of measuring a biometric signal when a user wears the electronic device 200 on his or her wrist.

Referring to FIG. 10A, if the user wears the electronic device 200 on his or her wrist, a second electrode (e.g., the second electrode 320 of FIGS. 3A and 3B) and a third electrode (e.g., the third electrode 330 of FIGS. 3A and 3B) disposed on the rear side (e.g., the second side 210B of FIGS. 2A and 2B) of the electronic device 200 may be in contact with the wrist of the user. The electronic device 200 may provide, on a display (e.g., the display device 160 of FIG. 1 or the display 220 of FIGS. 2A and 2B), guidance so that the user makes a contact of a body part of the user with a first electrode (e.g., the first electrode 310 of FIGS. 3A and 3B) disposed in the front side (e.g., the first side 210A of FIGS. 2A and 2B) or a lateral side (e.g., the lateral bezel structure 206 of FIGS. 2A and 2B) of the electronic device 200. For example, the user may wear the electronic device 200 on his or her left wrist 1010, and may make a contact of his or her right finger 1020 with the first electrode 310. The control circuit (e.g., the control circuit 380 of FIGS. 3A and 3B) may measure a biometric signal using signals received from the first electrode 310 and the second electrode 320.

FIG. 10B is a diagram illustrating an example of removing noise by adjusting a feedback gain and the area of an electrode.

Referring to FIG. 10B, a feedback gain control (or adjustment) process 1030 may be a process of adjusting the gain of a feedback amplifier (e.g., the feedback amplifier 370 of FIGS. 3A and 3B) based on noise of signals received via the first electrode 310 and the second electrode 320. A feedback noise output from the feedback amplifier 370 according to the adjustment of the gain may be feedback to the body of the user via the third electrode 330. The control circuit 380 may decrease the magnitude of noise based on the adjustment of the gain of the feedback amplifier 370. The electrode area control (or adjustment) process 1040 may adjust the number (or the area) of electrode nodes or the locations of the electrode nodes included in the first electrode 310 and the second electrode 320 based on noise of signals received via the first electrode 310 and the second electrode 320. The control circuit 380 may reduce the magnitude of noise by adjusting the number of the electrode nodes or the locations of the electrode nodes included in the first electrode 310 and the second electrode 320 which are provided in the forms of matrices.

According to certain embodiments, the control circuit 380 may perform both the feedback gain control process 1030 or the electrode area control process 1040. The control circuit 380 may perform the feedback gain control process 1030, and then, may perform the electrode area control process 1040. Alternatively, the reverse is possible. The control circuit 380 may perform one of the feedback gain control process 1030 or the electrode area control process 1040 selectively or as needed. The control circuit 380 may perform one of the feedback gain control process 1030 or the electrode area control process 1040 based on the magnitude of noise or the characteristic of noise included in a biometric signal.

FIG. 11 is a flowchart 1100 illustrating a method of measuring a biometric signal using an electrode by an electronic device according to certain embodiments.

Referring to FIG. 11, in operation 1101, the control circuit 380 (e.g., the processor 120 of FIG. 1) of an electronic device (e.g., the electronic device 101 of FIG. 1 or the electronic device 200 of FIGS. 2A and 2B) according to certain embodiments may measure a biometric signal. For example, a biometric signal may be measured using signals received from a first electrode (e.g., the first electrode 310 of FIGS. 3A and 3B) disposed in the front side (e.g., the first side 210A of FIGS. 2A and 2B) of the electronic device 200 or a second electrode (e.g., the second electrode 320 of FIGS. 3A and 3B) disposed in the rear side (e.g., the second side 210B of FIGS. 2A and 2B) of the electronic device 200.

In operation 1103, the control circuit 380 may analyze the biometric signal. Analyzing the biometric signal may be a process of analyzing how much noise is included in the biometric signal. Alternatively, analyzing the biometric signal may be a process of analyzing the characteristics of noise included in the biometric signal. The control circuit 380 may adjust a feedback gain or the area of an electrode according to the characteristic of the noise.

In operation 1105, the control circuit 380 may determine whether settings need to be changed. The settings to be changed may include a feedback gain or the area of an electrode. The control circuit 380 may determine whether the magnitude of noise included in the biometric signal exceeds a noise threshold value. For example, if the magnitude of the noise exceeds the noise threshold value (e.g., changing of the settings is needed), the control circuit 380 proceeds with operation 1109. If the magnitude of the noise is less than or equal to the noise threshold value (e.g., changing of the settings is not needed), the control circuit 380 may proceed with operation 1107.

If the settings do not need to be changed, the control circuit 380 may store biometric information in operation 1107. The control circuit 380 may produce at least one piece of biometric information among ECG, GSR, EEG, or BIA, using the measured biometric signal. The control circuit 380 may store the produced biometric information in a memory (e.g., the memory 130 of FIG. 1), or may provide the same to a user via a display (e.g., the display device 160 of FIG. 1).

If the settings need to be changed, the control circuit 380 may perform a set value control process based on the biometric signal in operation 1109. The set value control process may include a feedback gain control process or an electrode area control process. According to certain embodiments, the control circuit 380 may perform the feedback gain control process or the electrode area control process in parallel or sequentially. The control circuit 380 may perform both, or one of, the feedback gain control process and the electrode area control process, based on the magnitude of the noise or the characteristics of the noise. Alternatively, the control circuit 380 may perform one of the feedback gain control process and the electrode area control process preferentially or later, based on the magnitude of the noise or the characteristics of the noise.

Figure 12:
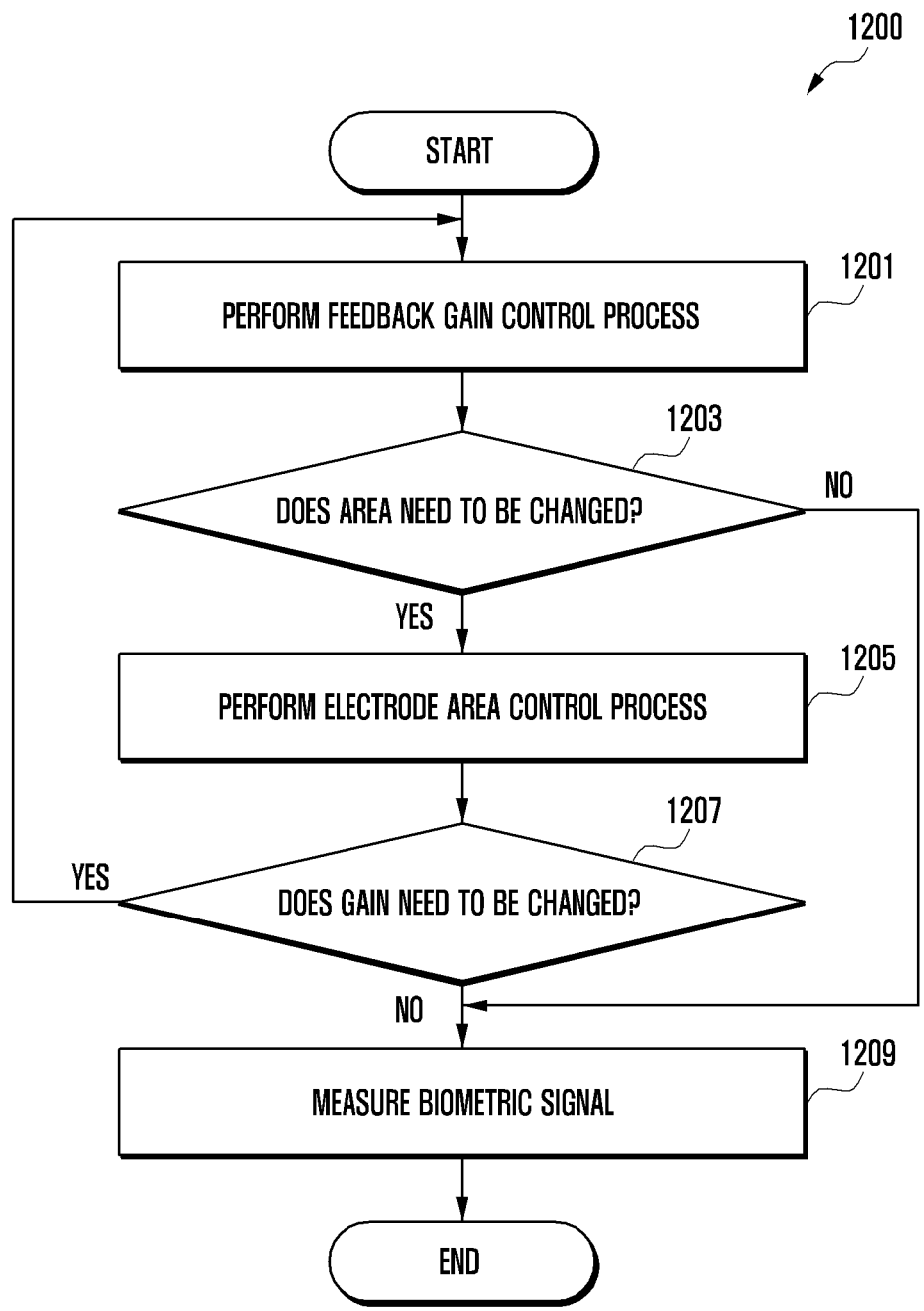
FIG. 12 is a flowchart 1200 illustrating a method of measuring a biometric signal using an electrode by an electronic device according to certain embodiments.

FIG. 12 is a flowchart 1200 illustrating a method of measuring a biometric signal using an electrode by an electronic device according to certain embodiments.

Referring to FIG. 12, in operation 1201, the control circuit 380 (e.g., the processor 120 of FIG. 1) of an electronic device (e.g., the electronic device 101 of FIG. 1 or the electronic device 200 of FIGS. 2A and 2B) according to certain embodiments may perform a feedback gain control process. The feedback gain control process may be a process of adjusting the gain of a feedback amplifier (e.g., the feedback amplifier 370 of FIGS. 3A and 3B) based on noise of signals received via a first electrode (e.g., the first electrode 310 of FIGS. 3A and 3B) and a second electrode (e.g., the second electrode 320 of FIGS. 3A and 3B). The feedback gain control process may include operations of FIG. 4.

In operation 1203, the control circuit 380 may determine whether the area of an electrode needs to be changed. The control circuit 380 may perform a feedback gain control process, and may determine whether noise is included in an obtained biometric signal. If the magnitude of noise included in the biometric signal exceeds a noise threshold value, the control circuit 380 may determine that the area of the electrode needs to be changed. If the area of the electrode needs to be changed, the control circuit 380 may perform operation 1205. If the area of the electrode does not need to be changed, the control circuit 380 may perform operation 1209.

If the area of the electrode needs to be changed, the control circuit 380 may perform an electrode area control process in operation 1205. If the first electrode 310 and the second electrode 320 are provided in the forms of matrices, the control circuit 380 may control the output of the multiplexer 340 so as to adjust the area of the electrode. For example, if the first electrode 310 and the second electrode 320 are provided in the forms of 2×3 matrices as shown in FIG. 8B, and operations 1201 to 1203 are performed, only a biometric signal measured by a 2×2 matrix (e.g., the first electrode node 851 to the fourth electrode node 854) may be output as an output of the multiplexer 340. The control circuit 380 may perform control so that the first electrode 310 and the second electrode 320 output all input values of the 3×3 matrices (e.g., the first electrode node 851 to the sixth electrode node 856) as an output of the multiplexer 340. The electrode area control process may include operations of FIG. 7.

In operation 1207, the control circuit 380 may determine whether a feedback gain needs to be changed. The control circuit 380 may perform the electrode area control process, and may determine whether noise is included in an obtained biometric signal. If the magnitude of noise included in the biometric signal exceeds a noise threshold value, the control circuit 380 may determine that the feedback gain needs to be changed. If the feedback gain needs to be changed, the control circuit 380 may return to operation 1201. If the feedback gain does not need to be changed, the control circuit 380 may proceed with operation 1209.

In operation 1209, the control circuit 380 may measure a biometric signal. The control circuit 380 sets a gain of the feedback amplifier 370 which makes the magnitude of noise to be decreased (or removed), and may measure (or produce) a biometric signal using a signal received via the first electrode 310 and the second electrode 320, the multiplexer 340, and the instrumentation amplifier 360. The control circuit 380 may measure (or produce) a biometric signal using signals received via the first electrode 310 and the second electrode 320 having areas which reduce the magnitude of noise, the multiplexer 340, and the instrumentation amplifier 360. The control circuit 380 may adjust the feedback gain and the area of the electrode, and may measure a biometric signal. The control circuit 380 may store biometric information which is produced using the measured biometric signal in a memory (e.g., the memory 130 of FIG. 1), or may provide the same to a user via a display (e.g., the display device 160 of FIG. 1).

An operation method of an electronic device including a first electrode (e.g., the first electrode 310 of FIGS. 3A and 3B), a second electrode (e.g., the second electrode 320 of FIGS. 3A and 3B), and a third electrode (e.g., the third electrode 330 of FIGS. 3A and 3B) according to certain embodiments of the disclosure may include: an operation of obtaining, using an instrumentation amplifier (e.g., the instrumentation amplifier 360 of FIGS. 3A and 3B), a biometric signal from signals received from the first electrode and the second electrode; an operation of feeding back a feedback noise to a body part of a user via the third electrode using a feedback amplifier (e.g., the feedback amplifier 370 of FIGS. 3A and 3B); an operation of analyzing the magnitude of noise using the biometric signal; and an operation of controlling the gain of the feedback amplifier based on a result of the analysis.

The operation of controlling the gain may include: an operation of suspending increasing the gain of the feedback amplifier if the magnitude of the noise included in the biometric signal is increased, and an operation of setting the gain of the feedback amplifier to a feedback gain used before the magnitude of the noise is increased.

The method may further include an operation of controlling the output of the multiplexer included in the electronic device based on the magnitude of noise included in a biometric signal obtained after the gain of the feedback amplifier is set.

The operation of controlling the output of the multiplexer may include: an operation of analyzing the magnitude of noise using at least two input signals output from the multiplexer, and an operation of adjusting the areas of the first electrode and the second electrode based on a result of the analysis.

The operation of adjusting the area may include: if a difference between noise signals included in the two input signals exceeds a reference value, an operation of adjusting the areas of the first electrode and the second electrode by controlling the output of the multiplexer.

The operation of controlling the output of the multiplexer may include: an operation of performing control so as to transfer all signals input from the first electrode and the second electrode to the instrumentation amplifier, or an operation of performing control so as to transfer part of the signals input from the first electrode and the second electrode to the instrumentation amplifier.

The certain embodiments of the disclosure provided in the specification and the accompanying drawings are just predetermined examples for easily describing the technical contents of the disclosure and helping understanding of the disclosure, but the disclosure is not limited thereto. Therefore, it should be construed that the scope of the disclosure includes all modifications or modified forms obtained based on the technical idea of the disclosure, in addition to the embodiments disclosed herein.

The invention claimed is:

1. An electronic device comprising:
a plurality of electrodes including a first electrode, a second electrode, and a third electrode;
an instrumentation amplifier configured to differentially amplify signals received from the first electrode and the second electrode;
a feedback amplifier configured to provide feedback noise to a body part of a user via the third electrode; and
a control circuit,
wherein the control circuit is configured to:
analyze a magnitude of a noise using a biometric signal obtained from the instrumentation amplifier by increasing the gain of the feedback amplifier,
control a gain of the feedback amplifier based on a result of the analysis,
suspend, if the magnitude of the noise included in the biometric signal increases, increasing the gain of the feedback amplifier, and
set the gain of the feedback amplifier to a feedback gain used before the magnitude of the noise increases.

2. The electronic device as claimed in claim 1, further comprising: a multiplexer disposed between the first and second electrodes and the instrumentation amplifier, the multiplexer configured to transfer outputs of the first electrode and the second electrode to the instrumentation amplifier.

3. The electronic device as claimed in claim 2, wherein the multiplexer is configured to transfer all signals input from the first electrode and the second electrode to the instrumentation amplifier, or to transfer a portion of signals input from the first electrode and the second electrode to the instrumentation amplifier.

4. The electronic device as claimed in claim 2, wherein the control circuit is configured to analyze a magnitude of a noise using at least two input signals output from the multiplexer, and to adjust a number of electrode nodes or locations of electrode nodes included in the first electrode and the second electrode based on a result of the analysis.

5. The electronic device as claimed in claim 4, wherein, when a difference between noise signals included in the two input signals exceeds a reference value, the control circuit is configured to adjust an area of the first electrode and an area of the second electrode by controlling an output of the multiplexer.

6. The electronic device as claimed in claim 2, wherein the control circuit is configured to control an output of the multiplexer based on a magnitude of a noise in a biometric signal obtained after the gain of the feedback amplifier is set.

7. The electronic device as claimed in claim 6, wherein, when the magnitude of the noise in the biometric signal exceeds a predetermined noise threshold value, the control circuit is configured to control the output of the multiplexer.

8. The electronic device as claimed in claim 1, wherein the first electrode is disposed in a foreside of the electronic device, and the second electrode and the third electrode are disposed in a rear side of the electronic device.

9. The electronic device as claimed in claim 1, wherein the first electrode and the third electrode are disposed in a foreside of the electronic device, and
the second electrode is disposed in a rear side of the electronic device.

10. An electronic device comprising:
a plurality of electrodes including a first electrode, a second electrode, and a third electrode;
a multiplexer is connected in parallel with the first electrode and the second electrode,
an instrumentation amplifier configured to differentially amplify a signal output from the multiplexer,
a feedback amplifier configured to provide feedback noise to a body part of a user via the third electrode; and
a control circuit,
wherein the control circuit is configured to:
analyze a magnitude of a noise using the signal output from the multiplexer, and
adjust an area of the first electrode and an area of the second electrode based on a result of the analysis.

11. The electronic device as claimed in claim 10, wherein the control circuit is configured to analyze a magnitude of a noise using at least two input signals output from the multiplexer, and to control an output of the multiplexer based on a result of the analysis.

12. The electronic device as claimed in claim 11, wherein, when a difference between noise signals included in the two input signals exceeds a reference value, the control circuit is configured to adjust an area of the first electrode and an area of the second electrode by controlling the output of the multiplexer.

13. An operation method of an electronic device including a first electrode, a second electrode, and a third electrode, the method comprising:
obtaining, using an instrumentation amplifier, a biometric signal from signals received from the first electrode and the second electrode;
feeding back a feedback noise to a body part of a user via the third electrode using a feedback amplifier;
analyzing a magnitude of a noise using the biometric signal by increasing the gain of the feedback amplifier; and
controlling a gain of the feedback amplifier based on a result of the analysis,
wherein the controlling the gain of the feedback amplifier comprises:
suspending, if the magnitude of the noise included in the biometric signal increases, increasing the gain of the feedback amplifier; and
setting the gain of the feedback amplifier to a feedback gain used before the magnitude of the noise increases.

* * * * *